(12) United States Patent
Kasuya et al.

(10) Patent No.: US 12,329,538 B2
(45) Date of Patent: *Jun. 17, 2025

(54) SYSTEM FOR IDENTIFYING INFORMATION REPRESENTED BY BIOLOGICAL SIGNALS

(71) Applicant: FrontAct Co., Ltd., Tokyo (JP)

(72) Inventors: Masahiro Kasuya, Tokyo (JP); Tatsuya Seki, Tokyo (JP)

(73) Assignee: FrontAct Co., Ltd., Tokyo (JP)

( * ) Notice: Subject to any disclaimer, the term of this patent is extended or adjusted under 35 U.S.C. 154(b) by 192 days.

This patent is subject to a terminal disclaimer.

(21) Appl. No.: 17/487,286

(22) Filed: Sep. 28, 2021

(65) Prior Publication Data

US 2022/0008003 A1    Jan. 13, 2022

Related U.S. Application Data

(63) Continuation of application No. 16/767,710, filed as application No. PCT/JP2018/044242 on Nov. 30, 2018, now Pat. No. 11,166,667.

(30) Foreign Application Priority Data

Nov. 30, 2017    (JP) ................ 2017-231054

(51) Int. Cl.
*A61F 2/72*    (2006.01)
*A61B 5/00*    (2006.01)
(Continued)

(52) U.S. Cl.
CPC .......... *A61B 5/4836* (2013.01); *A61B 5/4205* (2013.01); *A61B 5/6822* (2013.01);
(Continued)

(58) Field of Classification Search
None
See application file for complete search history.

(56) References Cited

U.S. PATENT DOCUMENTS

| 5,336,269 | A | 8/1994 | Smits |
| 11,166,667 | B2 * | 11/2021 | Kasuya ................ G16H 40/67 |

(Continued)

FOREIGN PATENT DOCUMENTS

| CN | 107072583 | 8/2017 |
| JP | 2001331250 A | 11/2001 |

(Continued)

OTHER PUBLICATIONS

First Office Action issued in Japanese Patent Application No. 2019-523894 dated Aug. 20, 2019 and its English translation.

(Continued)

*Primary Examiner* — David H Willse
(74) *Attorney, Agent, or Firm* — Renner, Otto, Boisselle & Sklar, LLP

(57) ABSTRACT

This system for identifying information represented by biological signals is configured so as to detect biological signals (S501), analyze the detected biological signals and then output feature data (S502), determine the respective similarities between the feature data and a plurality of teaching data (S503), store the similarities per time in a time series (S504), and determine information represented by the biological signals on the basis of the plurality of similarities within a prescribed period among the stored similarities in the time series (S505).

11 Claims, 14 Drawing Sheets

(51) Int. Cl.

| | | |
|---|---|---|
| *A61B 5/24* | (2021.01) | |
| *A61F 2/58* | (2006.01) | |
| *A61F 2/70* | (2006.01) | |
| *A61G 5/00* | (2006.01) | |
| *A61H 1/02* | (2006.01) | |
| *A63B 23/16* | (2006.01) | |
| *G06F 3/01* | (2006.01) | |
| *G16H 40/67* | (2018.01) | |
| *G16H 50/20* | (2018.01) | |
| *A61B 5/389* | (2021.01) | |
| *A61B 18/00* | (2006.01) | |
| *A61F 2/66* | (2006.01) | |

(52) U.S. Cl.
CPC .......... *A61B 5/6823* (2013.01); *A61B 5/6824* (2013.01); *A61B 5/6828* (2013.01); *A61B 5/7267* (2013.01); *A61F 2/583* (2013.01); *A61F 2/72* (2013.01); *A61G 5/00* (2013.01); *A61H 1/0237* (2013.01); *A61H 1/0274* (2013.01); *A61H 1/0292* (2013.01); *A63B 23/16* (2013.01); *G06F 3/015* (2013.01); *G16H 40/67* (2018.01); *G16H 50/20* (2018.01); *A61B 5/389* (2021.01); *A61B 2018/00839* (2013.01); *A61F 2002/6614* (2013.01); *A61F 2002/704* (2013.01); *A61H 2230/08* (2013.01); *A61M 2230/08* (2013.01); *A63B 2230/08* (2013.01)

(56) References Cited

U.S. PATENT DOCUMENTS

| | | |
|---|---|---|
| 2010/0174674 A1 | 7/2010 | Unuma et al. |
| 2010/0286748 A1 | 11/2010 | Midani et al. |
| 2012/0172744 A1 | 7/2012 | Kato et al. |
| 2016/0143751 A1 | 5/2016 | Chestek et al. |
| 2017/0172497 A1 | 6/2017 | Marquez Chin et al. |

FOREIGN PATENT DOCUMENTS

| | | |
|---|---|---|
| JP | 2010148604 A | 7/2010 |
| JP | 2017140198 A | 8/2017 |
| TW | 201309358 A1 | 3/2013 |
| WO | 2017073770 A1 | 5/2017 |

OTHER PUBLICATIONS

International Search Report for related International Application No. PCT/JP2018/044242 mailed Mar. 5, 2019.
Extended European Search Report for related European Application No. 18882992.3 dated Jul. 20, 2021.
First Office Action and search report for related Chinese Application No. 201880085716.2 dated Dec. 22, 2020 and English Translation.
Allowed claims of related U.S. Appl. No. 16/767,710, filed May 28, 2020.
First Office Action for corresponding Japanese Application No. 2020-008620 dated Feb. 2, 2023 and its English translation.
Communication pursuant to Article 94(3) EPC for corresponding European Application No. 18 882 992.3 dated Jun. 6, 2023.

* cited by examiner

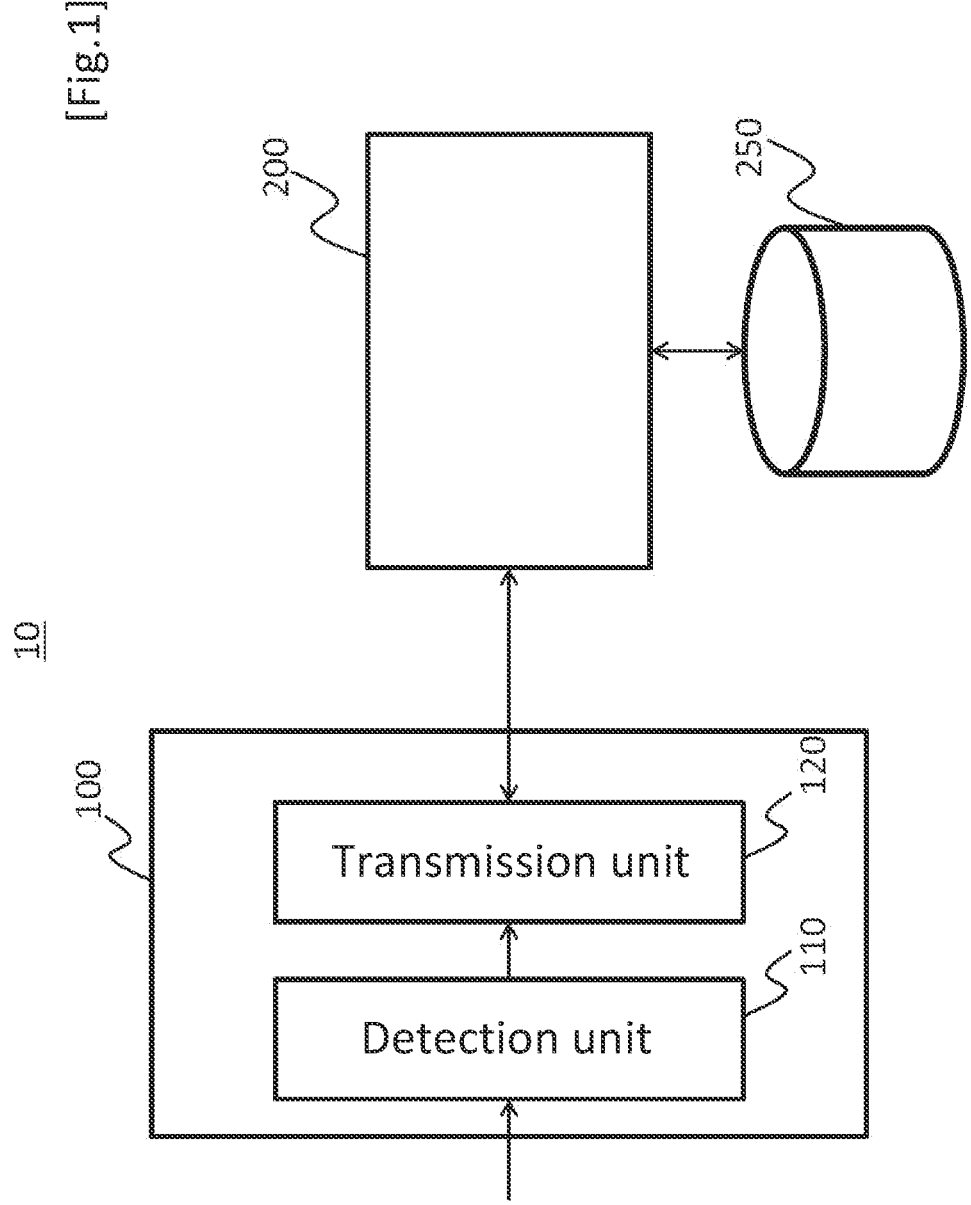

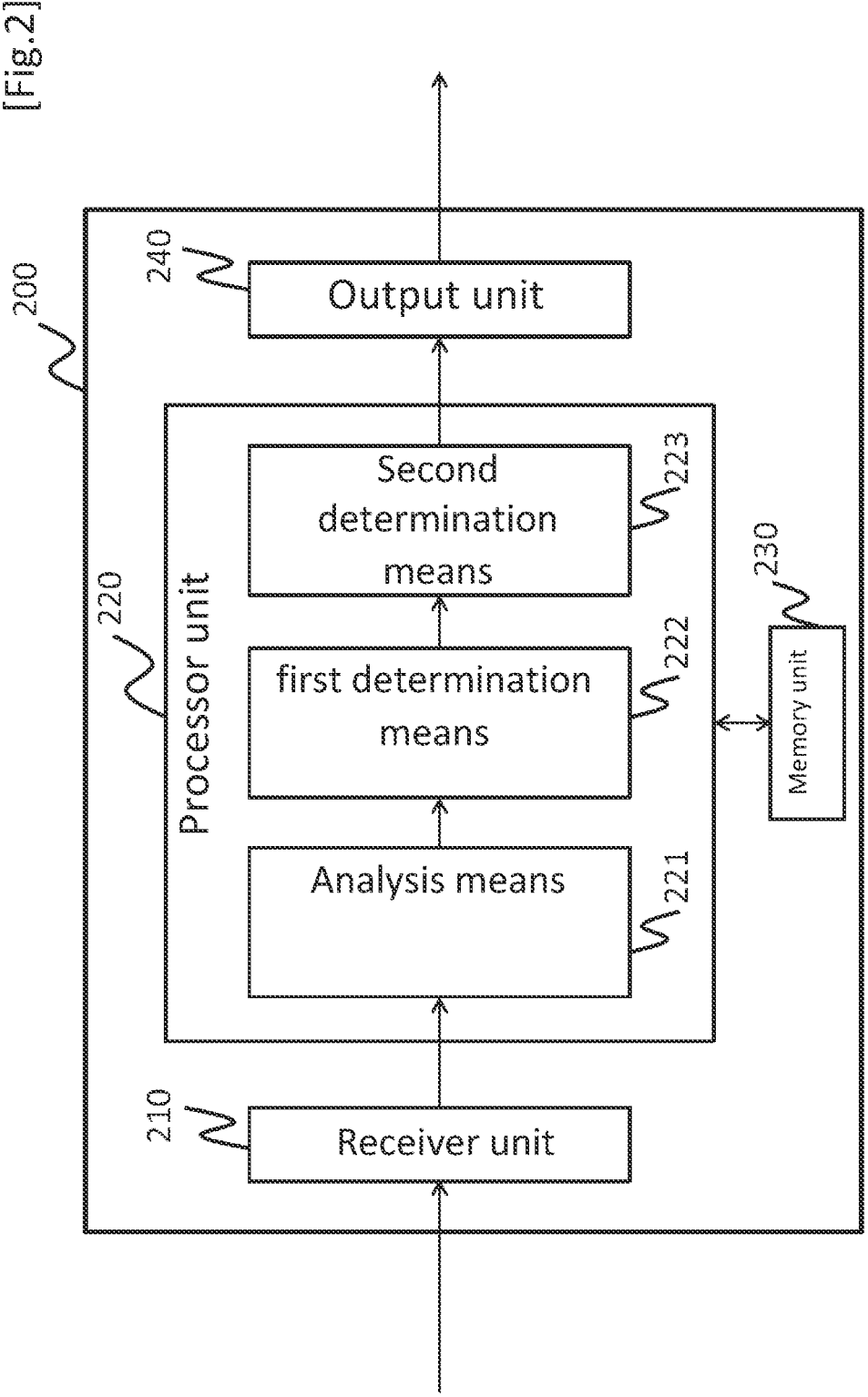
[Fig.2]

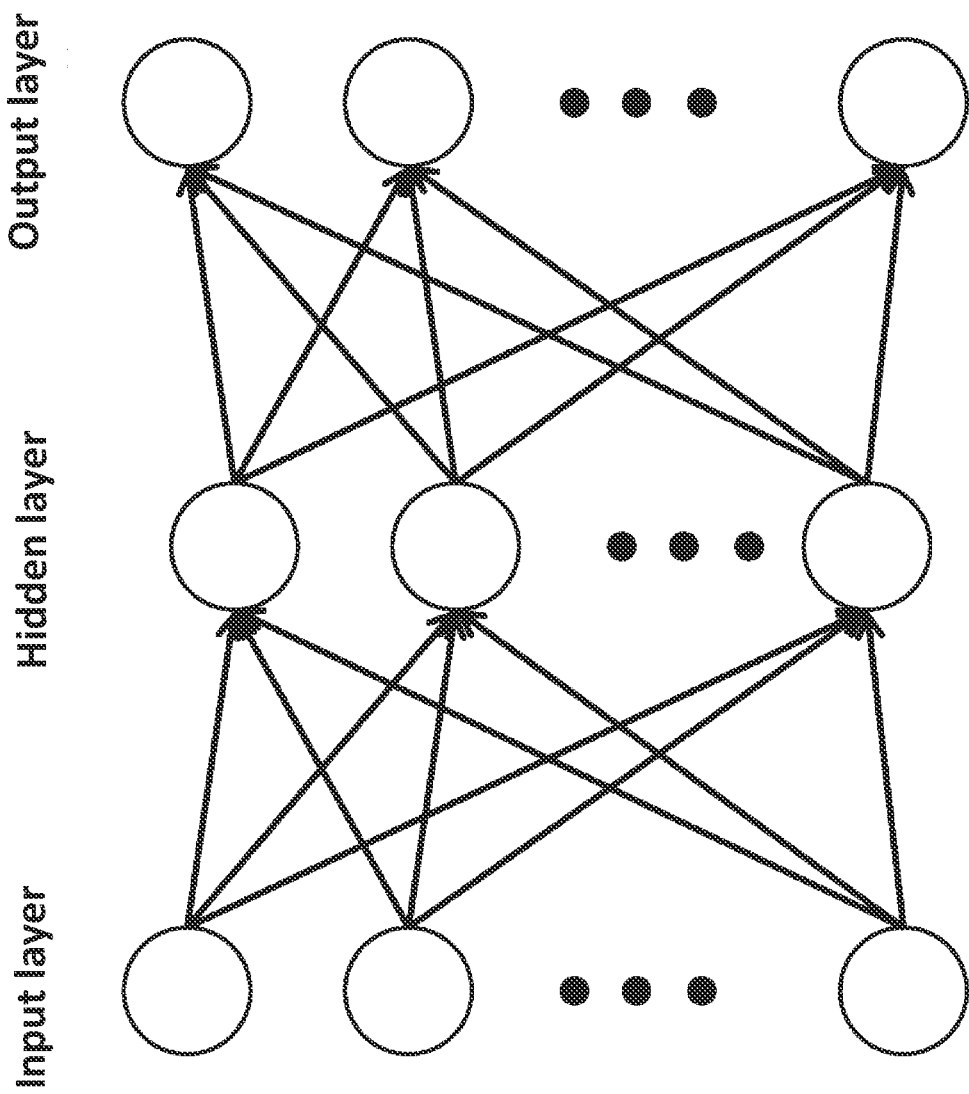

[Fig.4]

| Time<br>Output vector | 1 | 2 | 3 | 4 | 5 | 6 | 7 | 8 | 9 | 10 | ... |
|---|---|---|---|---|---|---|---|---|---|---|---|
| 0 | 0.0 | 0.0 | 0.0 | 0.0 | 0.0 | 0.0 | 0.0 | 0.0 | 0.0 | 0.0 | |
| 1 | 0.0 | 0.0 | 0.0 | 0.0 | 0.9 | 0.0 | 0.0 | 0.0 | 0.0 | 0.0 | |
| 2 | 0.2 | 0.2 | 0.2 | 0.2 | 0.2 | 0.2 | 0.2 | 0.2 | 0.2 | 0.2 | |
| 3 | 0.0 | 0.0 | 0.0 | 0.0 | 0.0 | 0.0 | 0.0 | 0.0 | 0.0 | 0.0 | |
| 4 | 0.5 | 0.0 | 0.0 | 0.0 | 0.0 | 0.0 | 0.0 | 0.0 | 0.0 | 0.0 | |
| 5 | 0.7 | 0.7 | 0.7 | 0.7 | 0.7 | 0.7 | 0.7 | 0.7 | 0.7 | 0.7 | |
| 6 | 0.0 | 0.9 | 0.0 | 0.0 | 0.0 | 0.9 | 0.0 | 0.0 | 0.0 | 0.0 | |
| 7 | 0.0 | 0.0 | 0.0 | 0.0 | 0.0 | 0.0 | 0.0 | 0.0 | 0.0 | 0.0 | |
| 8 | 0.0 | 0.0 | 0.0 | 0.0 | 0.0 | 0.0 | 0.0 | 0.9 | 0.0 | 0.0 | |
| 9 | 0.0 | 0.0 | 0.0 | 0.0 | 0.0 | 0.0 | 0.0 | 0.9 | 0.0 | 0.0 | |

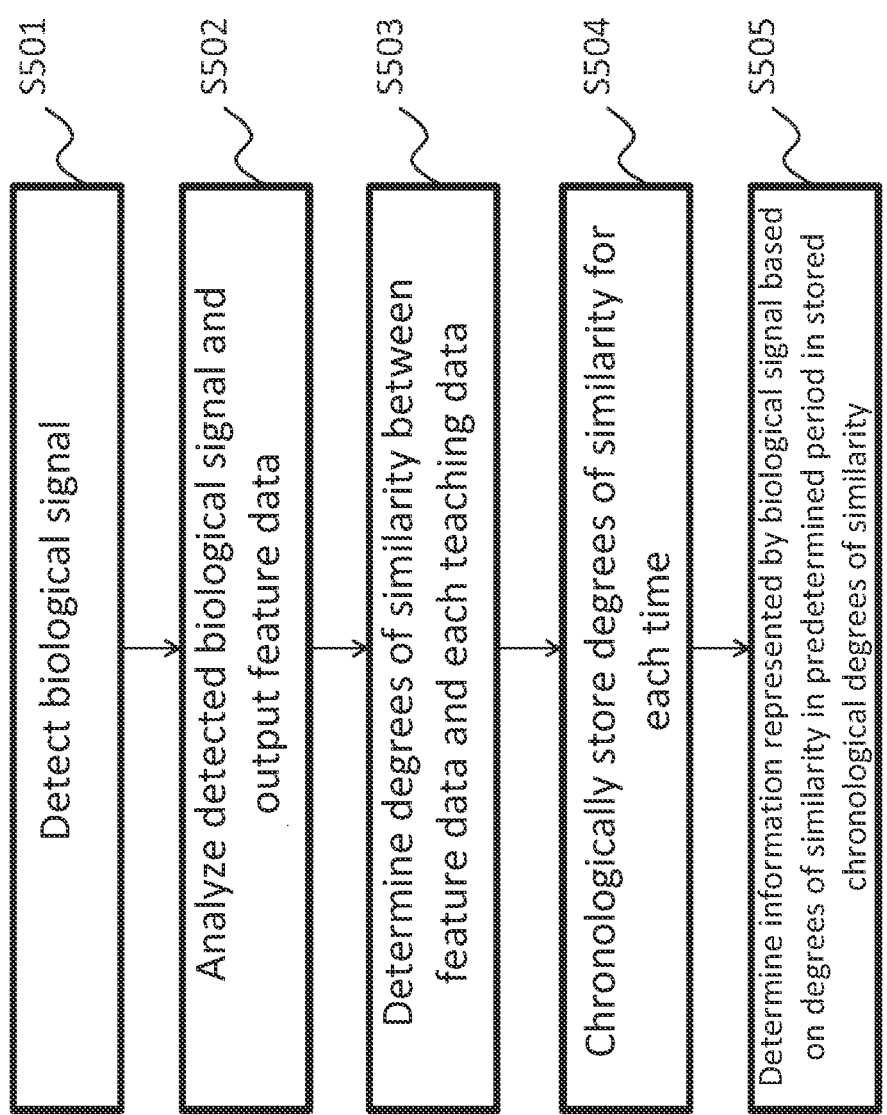

[Fig.6A]

| Output vector \ Time | 1 | 2 | 3 | 4 |
|---|---|---|---|---|
| 0 | 0.0 | 0.0 | 0.0 | 0.0 |
| 1 | 0.0 | 0.0 | 0.0 | 0.0 |
| 2 | 0.2 | 0.2 | 0.2 | 0.2 |
| 3 | 0.0 | 0.0 | 0.0 | 0.0 |
| 4 | 0.5 | 0.0 | 0.0 | 0.0 |
| 5 | 0.7 | 0.7 | 0.7 | 0.7 |
| 6 | 0.0 | 0.9 | 0.0 | 0.0 |
| 7 | 0.0 | 0.0 | 0.0 | 0.0 |
| 8 | 0.0 | 0.0 | 0.0 | 0.0 |
| 9 | 0.0 | 0.0 | 0.0 | 0.0 |

[Fig.6B]

| Output vector \ Time | 1 | 2 | 3 | 4 | 5 | → | Total |
|---|---|---|---|---|---|---|---|
| 0 | 0.0 | 0.0 | 0.0 | 0.0 | 0.0 | → | 0.0 |
| 1 | 0.0 | 0.0 | 0.0 | 0.0 | 0.9 | → | 0.9 |
| 2 | 0.2 | 0.2 | 0.2 | 0.2 | 0.2 | → | 1.0 |
| 3 | 0.0 | 0.0 | 0.0 | 0.0 | 0.0 | → | 0.0 |
| 4 | 0.5 | 0.0 | 0.0 | 0.0 | 0.0 | → | 0.5 |
| 5 | 0.7 | 0.7 | 0.7 | 0.7 | 0.7 | → | 3.5 |
| 6 | 0.0 | 0.9 | 0.0 | 0.0 | 0.0 | → | 0.9 |
| 7 | 0.0 | 0.0 | 0.0 | 0.0 | 0.0 | → | 0.0 |
| 8 | 0.0 | 0.0 | 0.0 | 0.0 | 0.0 | → | 0.0 |
| 9 | 0.0 | 0.0 | 0.0 | 0.0 | 0.0 | → | 0.0 |

[Fig.6C]

| Output vector \ Time | 1 | 2 | 3 | 4 | 5 | 6 | | Total |
|---|---|---|---|---|---|---|---|---|
| 0 |  | 0.0 | 0.0 | 0.0 | 0.0 | 0.0 | → | 0.0 |
| 1 |  | 0.0 | 0.0 | 0.0 | 0.9 | 0.0 | → | 0.9 |
| 2 |  | 0.2 | 0.2 | 0.2 | 0.2 | 0.2 | → | 1.0 |
| 3 |  | 0.0 | 0.0 | 0.0 | 0.0 | 0.0 | → | 0.0 |
| 4 |  | 0.0 | 0.0 | 0.0 | 0.0 | 0.0 | → | 0.0 |
| 5 |  | 0.7 | 0.7 | 0.7 | 0.7 | 0.7 | → | 3.5 |
| 6 |  | 0.9 | 0.0 | 0.0 | 0.0 | 0.9 | → | 0.9 |
| 7 |  | 0.0 | 0.0 | 0.0 | 0.0 | 0.0 | → | 0.0 |
| 8 |  | 0.0 | 0.0 | 0.0 | 0.0 | 0.0 | → | 0.0 |
| 9 |  | 0.0 | 0.0 | 0.0 | 0.0 | 0.0 | → | 0.0 |

[Fig.6D]

| Output vector \ Time | 1 | 2 | 3 | 4 |
|---|---|---|---|---|
| 0 | 0.1 | 0.0 | 0.1 | 0.0 |
| 1 | 0.0 | 0.0 | 0.0 | 0.0 |
| 2 | 0.2 | 0.2 | 0.2 | 0.2 |
| 3 | 0.8 | 0.7 | 0.8 | 0.8 |
| 4 | 0.5 | 0.0 | 0.0 | 0.0 |
| 5 | 0.5 | 0.0 | 0.0 | 0.2 |
| 6 | 0.0 | 0.0 | 0.0 | 0.0 |
| 7 | 0.7 | 0.9 | 0.9 | 0.9 |
| 8 | 0.0 | 0.0 | 0.0 | 0.0 |
| 9 | 0.0 | 0.0 | 0.0 | 0.1 |

[Fig.6E]

| Output vector \ Time | 1 | 2 | 3 | 4 | 5 | | Total |
|---|---|---|---|---|---|---|---|
| 0 | 0.1 | 0.0 | 0.1 | 0.0 | 0.0 | → | 0.2 |
| 1 | 0.0 | 0.0 | 0.0 | 0.0 | 0.0 | → | 0.0 |
| 2 | 0.2 | 0.2 | 0.2 | 0.2 | 0.2 | → | 1.0 |
| 3 | 0.8 | 0.7 | 0.8 | 0.8 | 0.9 | → | 4.0 |
| 4 | 0.5 | 0.0 | 0.0 | 0.0 | 0.2 | → | 0.5 |
| 5 | 0.5 | 0.0 | 0.0 | 0.2 | 0.1 | → | 0.8 |
| 6 | 0.0 | 0.0 | 0.0 | 0.0 | 0.0 | → | 0.0 |
| 7 | 0.7 | 0.9 | 0.9 | 0.9 | 0.8 | → | 4.2 |
| 8 | 0.0 | 0.0 | 0.0 | 0.0 | 0.0 | → | 0.0 |
| 9 | 0.0 | 0.0 | 0.0 | 0.1 | 0.9 | → | 1.0 |

[Fig.6F]

| Output vector \ Time | 1 | 2 | 3 | 4 | 5 | 6 | | Total |
|---|---|---|---|---|---|---|---|---|
| 0 | 0.1 | 0.0 | 0.1 | 0.0 | 0.0 | 0.2 | → | 0.3 |
| 1 | 0.0 | 0.0 | 0.0 | 0.0 | 0.0 | 0.9 | → | 0.9 |
| 2 | 0.2 | 0.2 | 0.2 | 0.2 | 0.2 | 0.2 | → | 1.0 |
| 3 | 0.8 | 0.7 | 0.8 | 0.8 | 0.9 | 0.7 | → | 3.9 |
| 4 | 0.5 | 0.0 | 0.0 | 0.0 | 0.2 | 0.3 | → | 0.5 |
| 5 | 0.5 | 0.0 | 0.0 | 0.2 | 0.1 | 0.1 | → | 0.4 |
| 6 | 0.0 | 0.0 | 0.0 | 0.0 | 0.0 | 0.0 | → | 0.0 |
| 7 | 0.7 | 0.9 | 0.9 | 0.9 | 0.8 | 0.7 | → | 4.2 |
| 8 | 0.0 | 0.0 | 0.0 | 0.0 | 0.0 | 0.0 | → | 0.0 |
| 9 | 0.0 | 0.0 | 0.0 | 0.1 | 0.9 | 0.1 | → | 1.1 |

[Fig.7A]
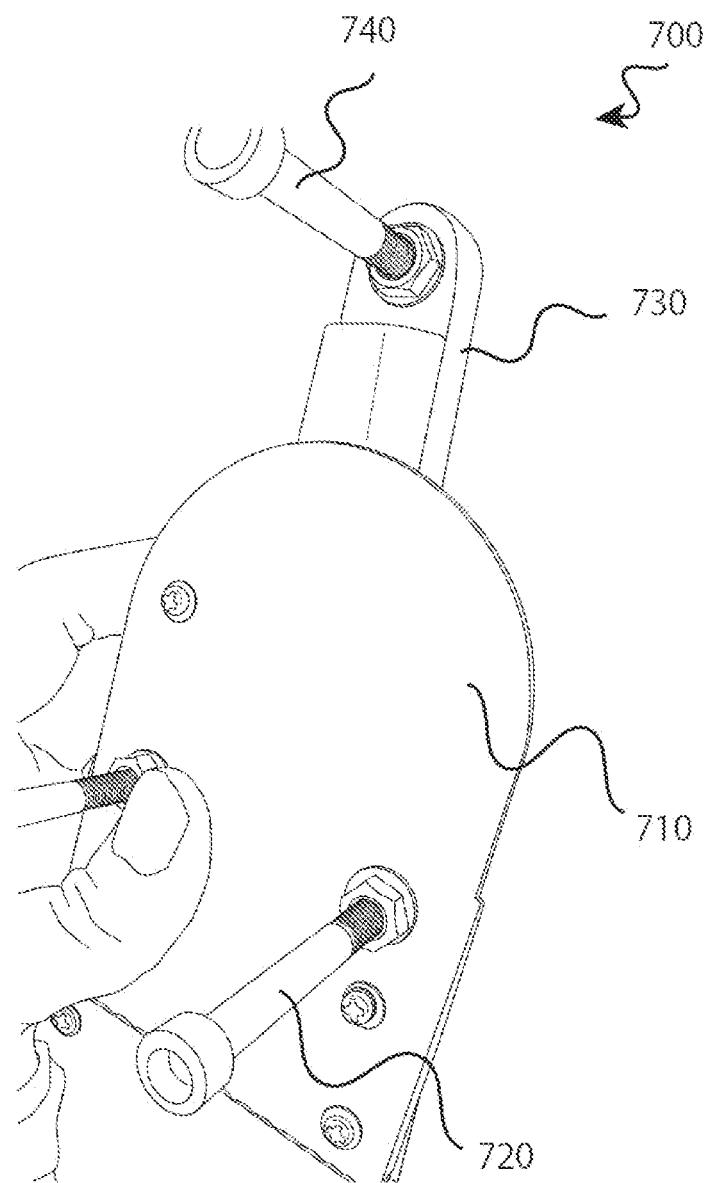

[Fig.7B]
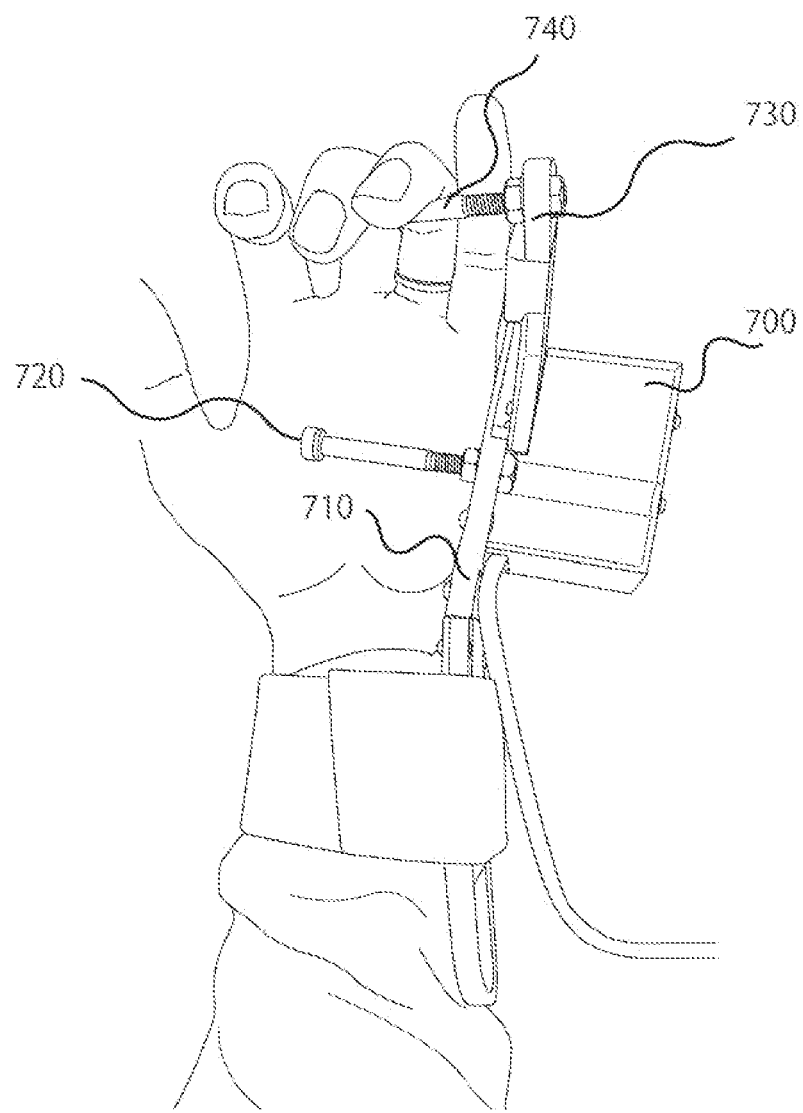

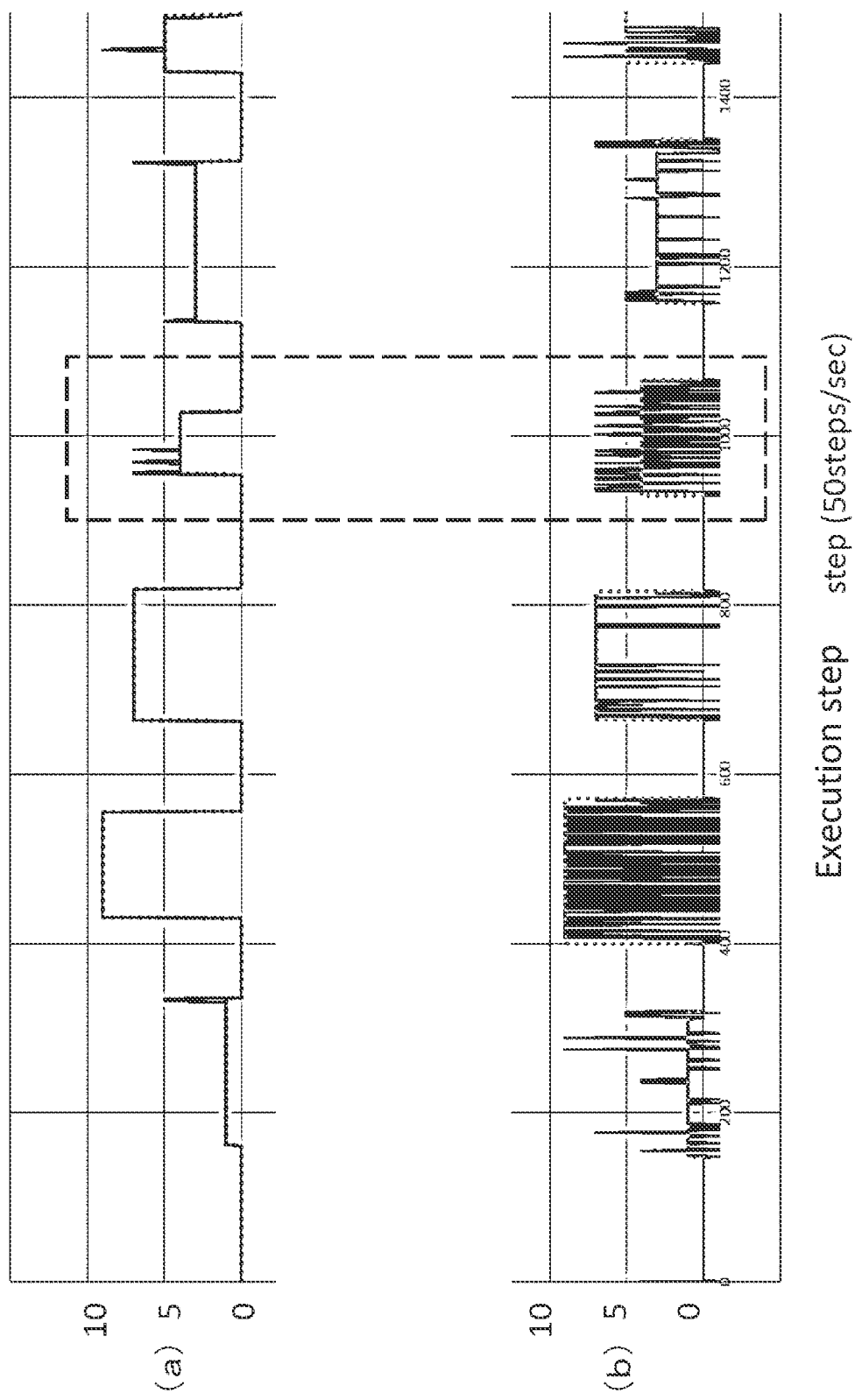

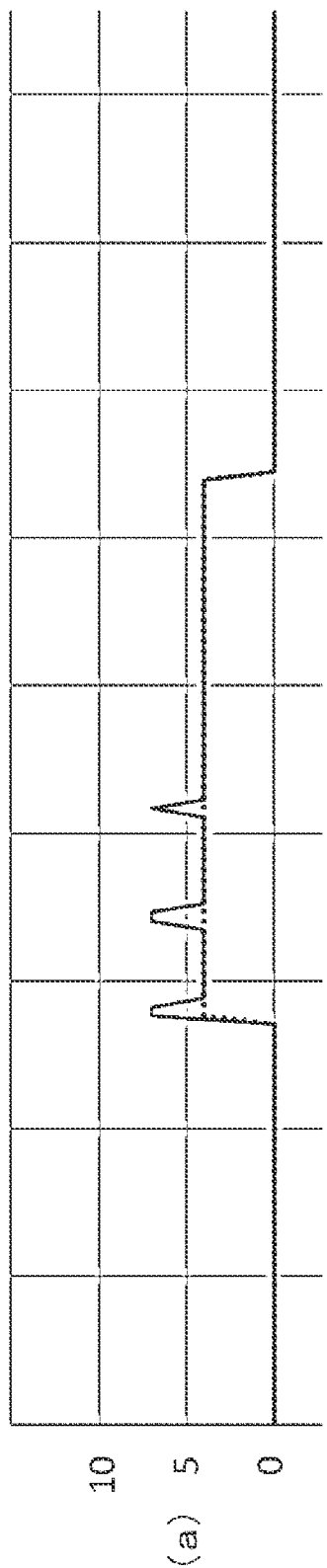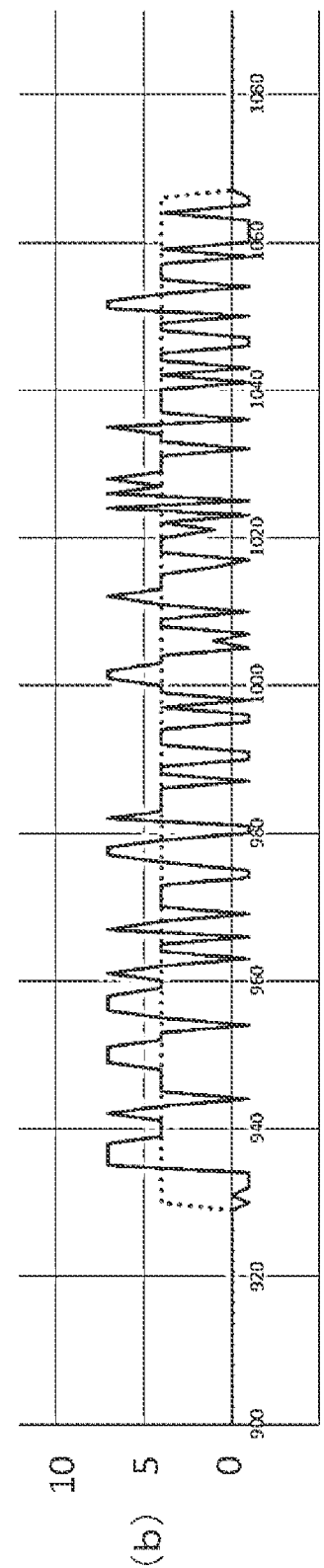
[Fig.9]

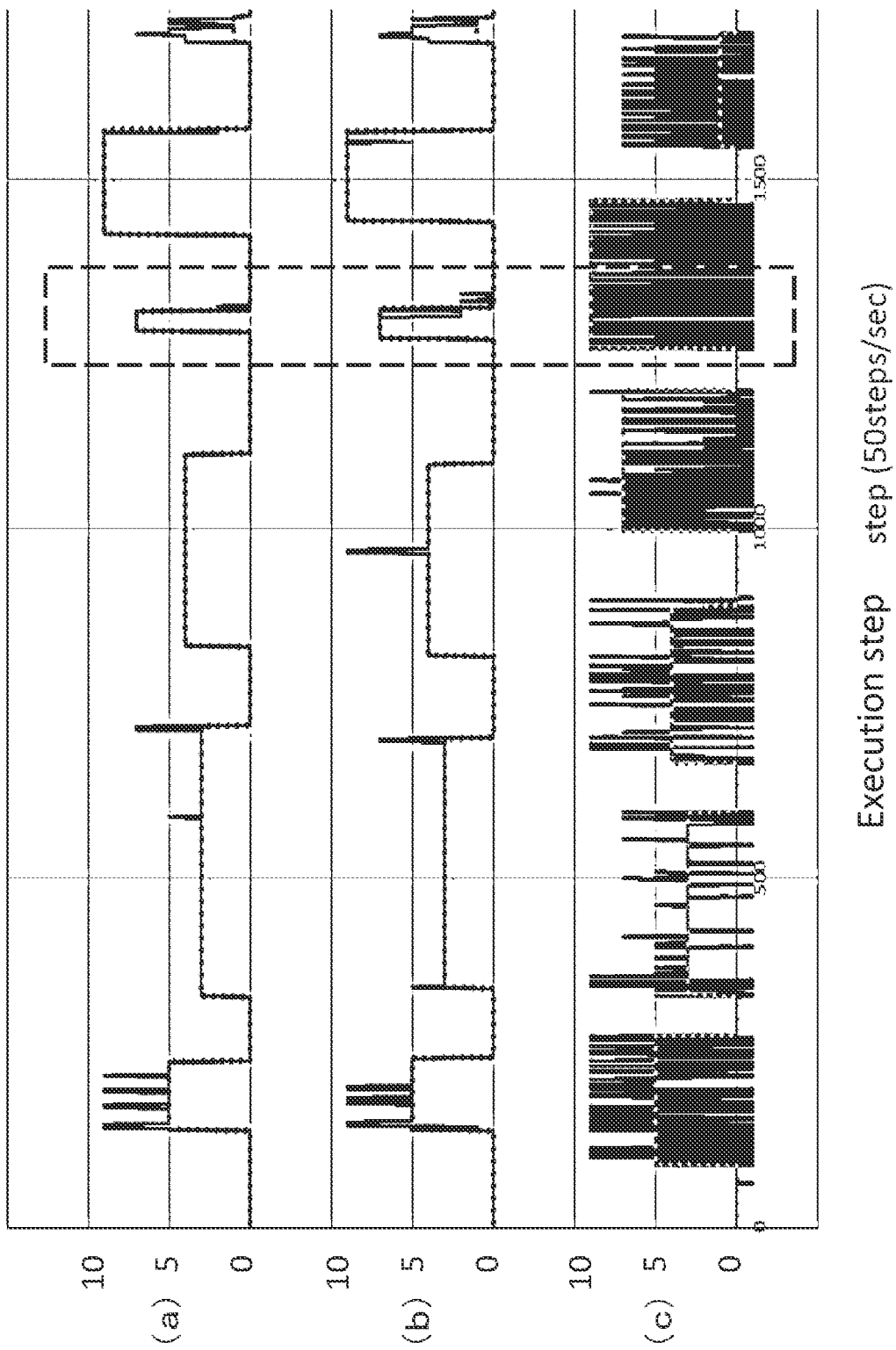

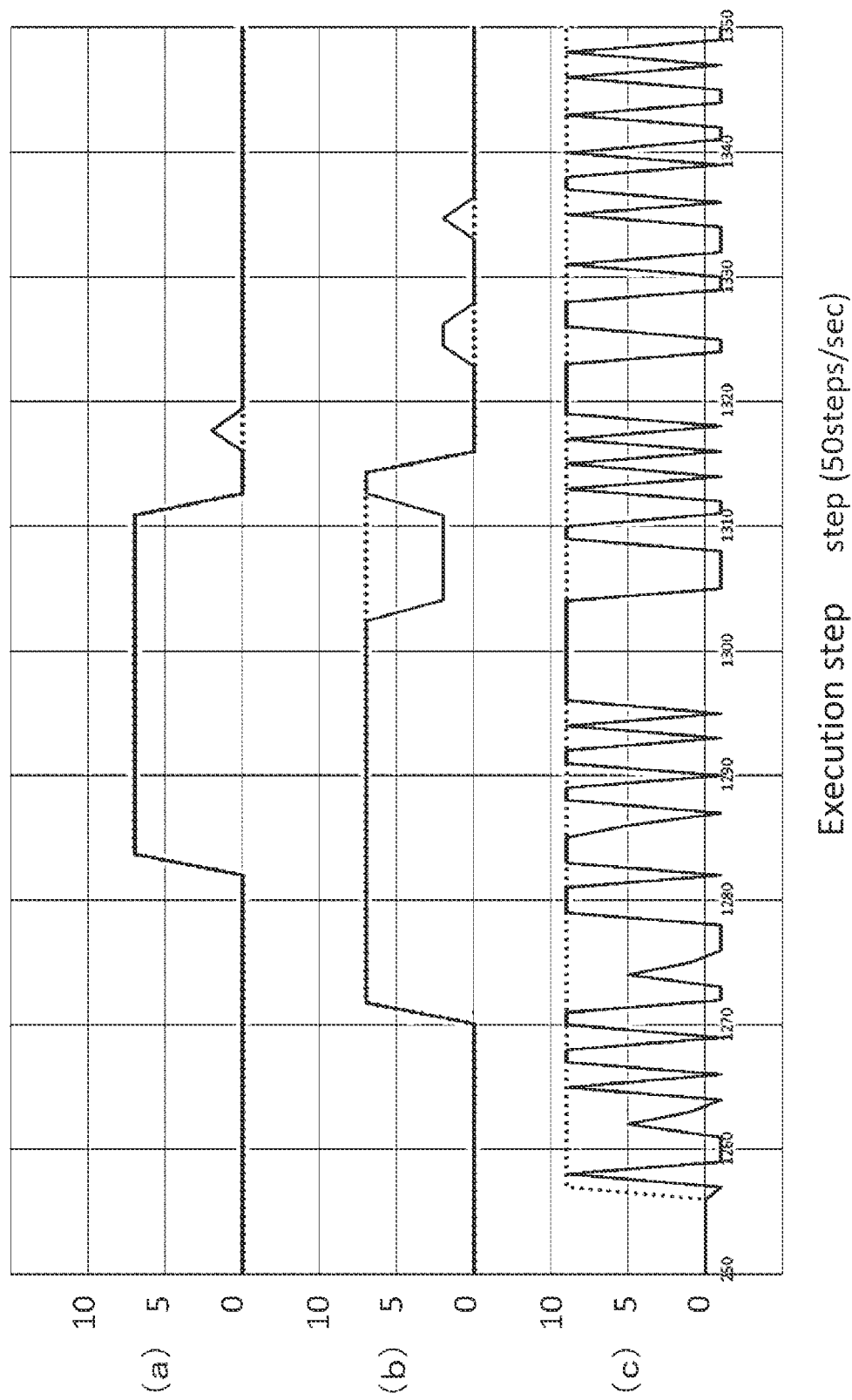

SYSTEM FOR IDENTIFYING INFORMATION REPRESENTED BY BIOLOGICAL SIGNALS

TECHNICAL FIELD

The present invention relates to a system for identifying information represented by a biological signal.

BACKGROUND ART

Efforts to use biological signals such as myoelectric signals to control equipment such as wheelchairs, prosthetic hands, and prosthetic feet have been ongoing (Patent Literature 1).

CITATION LIST

Patent Literature

[PTL 1] Japanese Laid-Open Publication No. 2001-331250

SUMMARY OF INVENTION

Technical Problem

However, precision to identify the motion represented by a biological signal such as a myoelectric signal is still not adequate. The precision of identification is low, especially when the level of biological signal is low or when biological signals of a plurality of motions coexist.

The objective of the present invention is to provide a system for identifying information represented by a biological signal, which enables enhanced precision to identify a biological signal to solve the aforementioned problem. Another objective is to provide a finger rehabilitation apparatus and a swallow diagnosis apparatus that apply the system for identifying information represented by a biological signal in the field of rehabilitation or diagnosis.

Solution to Problem

The present invention provides, for example, the following items.
(Item 1)
A system for identifying information represented by a biological signal, the system comprising:
  detection means for detecting a biological signal;
  analysis means for analyzing the detected biological signal and outputting feature data;
  first determination means for determining degrees of similarity between the feature data and each of a plurality of teaching data;
  storage means for chronologically storing the degrees of similarity for each time; and
  second determination means for determining information represented by the biological signal based on a plurality of degrees of similarity within a predetermined period in the chronological degrees of similarity stored in the storage means.
(Item 2)
The system of item 1, wherein the second determination means:
  calculates computed values for each of the plurality of teaching data based on the plurality of degrees of similarity within the predetermined period; and
  extracts teaching data corresponding to the highest computed value among the computed values and determines information indicated by the extracted teaching data as the information represented by the biological signal.
(Item 3)
The system of item 1, wherein the second determination means:
  calculates computed values for each of the plurality of teaching data based on the plurality of degrees of similarity within the predetermined period; and
  extracts at least one teaching data corresponding to a computed value exceeding a predetermined threshold value among the computed values and determines information indicated by the extracted teaching data as the information represented by the biological signal.
(Item 4)
The system of item 3, wherein the second determination means extracts a plurality of teaching data corresponding to computed values exceeding the predetermined threshold value among the computed values and determines information indicated by each of the plurality of extracted teaching data as the information represented by the biological signal.
(Item 5)
The system of item 4, wherein the information represented by the biological signal indicates that a composite motion has been performed.
(Item 6)
The system of any one of items 2 to 5, wherein the computed values are total values.
(Item 7)
The system of any one of items 1 to 6, wherein the storage means is a buffer for temporarily storing information, and the degrees of similarity are temporarily stored in the buffer.
(Item 8)
The system of any one of items 1 to 7, wherein the predetermined period is about 80 to 200 ms.
(Item 9)
The system of any one of items 1 to 8, further comprising wearing means for wearing the detection means on a body of a subject.
(Item 10)
The system of item 9, wherein the body is an upper limb, an abdomen, a neck, a lower limb, or a back of the subject.
(Item 11)
The system of any one of items 1 to 10 for finger rehabilitation, for swallow diagnosis, for a wheelchair, for a prosthetic hand, for a prosthetic arm, for a prosthetic foot, for a robot, for an upper limb assisting apparatus, for a lower limb assisting apparatus, or for a trunk assisting apparatus.
(Item 12)
A finger rehabilitation apparatus comprising:
  the system of any one of items 1 to 11; and
  a finger movement assisting apparatus.
(Item 13)
A swallow diagnosis apparatus comprising the system of any one of items 1 to 11.

Advantageous Effects of Invention

The present invention can provide a system for identifying information represented by a biological signal, which enables enhanced precision to identify a biological signal. The present invention can also provide a finger rehabilitation apparatus and a swallow diagnosis apparatus that apply the system for identifying information represented by a biological signal in the field of rehabilitation or diagnosis.

BRIEF DESCRIPTION OF DRAWINGS

FIG. 1 is a diagram showing an example of a configuration of the system 10 for identifying information represented by a biological signal of the invention.

FIG. 2 is a diagram showing an example of a configuration of a computer apparatus 200.

FIG. 3 is a diagram showing an example of a configuration of a neural network 300 used by first determination means 222.

FIG. 4 is a diagram showing an example of a data configuration of degrees of similarity stored in a buffer of a memory unit 230.

FIG. 5 is a flow chart showing an example of the processing for identifying information represented by a biological signal of the invention.

FIG. 6A is a diagram showing an example of degrees of similarity stored in a buffer of a memory unit 230.

FIG. 6B is a diagram explaining that second determination means 223 obtains total values by totaling a plurality of degrees of similarity within a predetermined period in chronological degrees of similarity stored in a buffer for each teaching data.

FIG. 6C is a diagram explaining that second determination means 223 obtains total values by totaling a plurality of degrees of similarity within a predetermined period in chronological degrees of similarity stored in a buffer for each teaching data.

FIG. 6D is a diagram showing another example of degrees of similarity stored in a buffer of the memory unit 230.

FIG. 6E is a diagram explaining that second determination means 223 obtains total values by totaling a plurality of degrees of similarity within a predetermined period in chronological degrees of similarity stored in a buffer for each teaching data.

FIG. 6F is a diagram explaining that second determination means 223 obtains total values by totaling a plurality of degrees of similarity within a predetermined period in chronological degrees of similarity stored in a buffer for each teaching data.

FIG. 7A is a diagram showing the outer appearance of finger movement assisting apparatus 700.

FIG. 7B is a diagram showing the finger movement assisting apparatus 700 worn on a finger of a user.

FIG. 8 is a graph showing results of an experiment for identifying a motion represented by a myoelectric signal detected from a myoelectric sensor that is worn on the skin of an upper limb of a subject.

FIG. 9 is a graph expanding the dotted line portion of the graph in FIG. 8.

FIG. 10 is a graph showing results of a test for identifying a motion represented by a myoelectric signal detected from a myoelectric sensor that is worn on the skin of an upper limb of a subject with a low level of myoelectric signal.

FIG. 11 is a graph expanding the dotted line portion of the graph in FIG. 10.

DESCRIPTION OF EMBODIMENTS

The present invention is described hereinafter. The terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

1. Definitions of the Terms

As used herein, "biological signal" refers to a signal emitted by an organism. Examples of biological signals include, but are not limited to, myoelectric signals indicating the activity of a muscle of an organism, cardioelectric signals indicating the activity of the heart of an organism, brainwaves indicating the activity of a brain of an organism, neural signals transmitted in neurons, and the like. Biological signals as used herein refers to a scalar quantity extracted from measured biological signals in a broad sense. Use of biological signals in scalar quantity eliminates coordinate dependency, so that very high versatility and convenience can be attained. A specific value of a biological signal can be associated with specific information (e.g., a specific motion of an organism (hand grasping motion, hand opening motion, laughing motion, etc.) or a specific condition of an organism (e.g., degree or type of muscle fatigue, etc.)) herein.

As used herein, "feature data" refers to multidimensional data obtained by analyzing a biological signal in a scalar quantity.

As used herein, "teaching signal" refers to a signal for teaching that a specific value of a biological signal represents specific information. For example, a teaching signal can teach that a specific value of a biological signal represents a specific motion of an organism. For example, a teaching signal can teach that a specific value of a biological signal represents a specific condition of an organism.

As used herein, "teaching data" refers to multidimensional data corresponding to a teaching signal. The dimensionality of teaching data corresponds to the number of pieces of information to be identified. If, for example, five pieces of information are taught, the dimensionality of teaching data is at least five, and the teaching data is represented by (a, b, c, d, e) ($0 \leq a, b, c, d, e \leq 1$). For example, teaching data 1 corresponding to teaching signal "1", which teaches that the information is the first information, can be (1.0, 0.0, 0.0, 0.0, 0.0), teaching data 2 corresponding to teaching signal "2", which teaches that the information is the second information, can be (0.0, 1.0, 0.0, 0.0, 0.0), teaching data 3 corresponding to teaching signal "3", which teaches that the information is the third information, can be (0.0, 0.0, 1.0, 0.0, 0.0), teaching data 4 corresponding to teaching signal "4", which teaches that the information is the fourth information, can be (0.0, 0.0, 0.0, 1.0, 0.0), and teaching data 5 corresponding to teaching signal "5", which teaches that the information is the fifth information, can be (0.0, 0.0, 0.0, 0.0, 1.0).

As used herein, "about" means that the number described after said term is within the range of the number ±10%.

The embodiments of the invention are described hereinafter with reference to the drawings.

2. Configuration of the System for Identifying Information Represented by Biological Signal of the Invention FIG. 1 shows an example of a configuration of the system 10 for identifying information represented by a biological signal of the invention. The system 10 comprises biological signal detection means 100 and a computer apparatus 200.

The biological signal detection means 100 can be any means configured to detect a biological signal and output the detected biological signal. For example, the biological signal detection means 100 can be a myoelectric device comprising a myoelectric sensor capable of detecting a myoelectric signal of an organism, an electrocardiograph comprising a cardioelectric sensor capable of detecting a cardioelectric signal of an organism, a brainwave meter comprising a brainwave sensor capable of detecting a brainwave of an organism, or the like. The biological signal detection means 100 can be configured to extract a scalar quantity from a detected biological signal and output the scalar quantity if the detected biological signal is a biological signal with coordinate dependency (e.g., if the detected brainwave is a vector quantity (of coordinates of measurement location, intensity), if a myoelectric signal detected at an electrode on a film is a vector quantity (of coordinates of measurement location, intensity), or the like). A database unit 250 is connected to the computer apparatus 200. The biological signal detection means 100 and the computer apparatus 200 can be connected in any manner. For example, the biological signal detection means 100 and the computer apparatus 200 can have a wired or wireless connection. For example, the biological signal detection means 100 and the computer apparatus 200 can be connected via a network (e.g., Internet, LAN, or the like). The computer apparatus 200 can be, for example, a computer apparatus that is used together with the biological signal detection means 100 or a remote server apparatus located away from the biological signal detection means 100.

The biological signal detection means 100 comprises a detection unit 110 and a transmission unit 120.

The detection unit 110 can be any means configured to detect a biological signal. For example, the detection unit 110 can be a myoelectric sensor capable of detecting a myoelectric signal of an organism, a cardioelectric sensor capable of detecting a myoelectric signal of an organism, a brainwave sensor capable of detecting a brainwave of an organism, or the like. If, for example, the detection unit 110 is a myoelectric sensor, the detection unit can comprise a primary amplifier, a high pass filter, a low pass filter, a notch filter, and a secondary amplifier for the detection of myoelectric signals. Primary and secondary amplifiers are used for amplifying a signal. A high pass filter is used for attenuating a signal with a frequency lower than a predetermined frequency, such as a signal with a frequency lower than about 10 Hz. A low pass filter is used for attenuating a signal with a frequency higher than a predetermined frequency, such as a signal with a frequency higher than about 500 Hz. A notch filter is used for attenuating a 50 to 60 Hz AC noise, which is a typical electrical noise. A band elimination filter can also be used in place of a notch filter.

The transmission unit 120 is configured to be capable of transmitting a signal out of the biological signal detection means 100. The transmission unit 120 transmits a signal out of the biological signal detection means 100 via a wireless or wired connection. For example, the transmission unit 120 can transmit a signal by utilizing a wireless LAN such as Wi-Fi. The transmission unit 120 can transmit a signal by utilizing a short range wireless communication or the like such as Bluetooth®. For example, the transmission unit 120 transmits a biological signal detected by the detection unit 110 to the computer apparatus 200.

For example, teaching data corresponding to a teaching signal inputted during the learning stage can be stored in the database unit 250 while being associated with inputted feature data. If, for example, a teaching signal is inputted by a user during the usage stage, teaching data corresponding to the inputted teaching signal can be stored in the database unit 250 while being associated with the feature data at the time.

FIG. 2 shows an example of a configuration of the computer apparatus 200.

The computer apparatus 200 comprises a receiver unit 210, a processor unit 220, a memory unit 230, and an output unit 240.

The receiver unit 210 is configured to be capable of receiving a signal from the outside of the computer apparatus 200. The receiver unit 210 receives a signal from the outside of the computer apparatus 200 via a wireless or wired connection. The receiver unit 210 can receive a signal by utilizing a wireless LAN such as Wi-Fi. The receiver unit 210 can receive a signal by utilizing a short range wireless communication or the like such as Bluetooth®. The receiver unit 210 receives a biological signal detected by the biological signal detection unit 100 from the biological signal detection unit 100. For example, the receiver unit 210 receives information stored in the database unit 250 from the database unit 250. The receiver unit 210 receives, for example, teaching signals for various information.

The processor unit 220 controls the operation of the entire computer apparatus 200. The processor unit 220 reads out a program stored in the memory unit 230 and executes the program. This allows the computer apparatus 200 to function as an apparatus that executes a desired step.

The memory unit 230 stores a program required to execute processing, data required to execute the program, and the like. For example, a program for materializing processing for identifying information represented by a biological signal (e.g., processing discussed below in FIG. 5) can be stored in the memory unit 230. In this regard, the program can be stored in the memory unit 230 in any manner. For example, a program can be preinstalled in the memory unit 230. Alternatively, a program can be installed in the memory unit 230 by downloading the program through a network, or installed in the memory unit 230 via a storage medium such as an optical disk or USB.

The output unit 240 is configured to be capable of outputting a single out of the computer apparatus 200. The output unit 240 can output a signal to anywhere. The output unit 240 can output a signal to any hardware or software. The output unit 240 can output a signal in any manner. For example, the output unit 240 can transmit a signal out of the computer apparatus 200 via a wired or wireless connection. For example, the output unit 240 can transmit a signal by converting the signal in a format that is compatible with the destination hardware or software, or by adjusting the signal to a response rate that is compatible with the destination hardware or software.

The processor unit 220 comprises analysis means 221, first determination means 222, and second determination means 223.

The analysis means 221 is configured to analyze a biological signal received by the receiver unit 210 and output feature data. Since the biological signal is in a scalar quantity such as potential, absolute amount of information is low. A large quantity of information can be identified by analyzing a biological signal with the analysis means 221 and producing feature data, which is multidimensional data. The analysis means 221 can perform, for example, analysis and processing including smoothing, mathematical analysis such as frequency analysis, and parameter determination, on biological signals.

The first determination means 222 is configured to determine degrees of similarly between feature data outputted by the analysis means 221 and each of a plurality of teaching data. A plurality of teaching data is stored in the database unit 250. For example, the first determination means 222 determines degrees of similarity between feature data and each of a plurality of teaching data from an output of a neural network. A neural network can be, for example, a feedforward neural network shown in FIG. 3.

FIG. 3 shows an example of a configuration of a neural network 300 used by the first determination means 222. The neural network 300 has an input layer, a hidden layer, and an output layer. The example in FIG. 3 shows the neural network 300 as a tri-layer feedforward neural network with one layer of hidden layer, but the number of hidden layers is not limited thereto. The neural network 300 can comprise one or more hidden layers. The number of nodes of the input layer of the neural network 300 corresponds to the dimensionality of feature data. The number of nodes of the output layer of the neural network 300 corresponds to the dimensionality of teaching data, i.e., corresponds to the number of pieces of information to be identified. The hidden layer of the neural network 300 can comprise any number of nodes. A weighting coefficient of each node of the hidden layer of the neural network 300 can be calculated based on a combination of feature data and teaching data stored in the database unit 250. For example, a weighting coefficient of each node can be calculated so that a value of the output layer when feature data is inputted into the input layer is a value of the teaching data associated with the feature data. This can be performed for example by backpropagation (backward propagation of errors).

Each node of the output layer of the neural network 300 where the weighting coefficient of each node is calculated in this manner is associated with information corresponding to each teaching data. For example, if the weighting coefficient for each node is calculated using a combination of feature data obtained from a biological signal generated from a first motion and teaching data 1 (1.0, 0.0, 0.0, 0.0, 0.0) corresponding to teaching signal "1" teaching that the motion is a first motion, a combination of feature data obtained from a biological signal generated from a second motion and teaching data 2 (0.0, 1.0, 0.0, 0.0, 0.0) corresponding to teaching signal "2" teaching that the motion is a second motion, a combination of feature data obtained from a biological signal generated from a third motion and teaching data 3 (0.0, 0.0, 1.0, 0.0, 0.0) corresponding to teaching signal "3" teaching that the motion is a third motion, a combination of feature data obtained from a biological signal generated from a fourth motion and teaching data 4 (0.0, 0.0, 0.0, 1.0, 0.0) corresponding to teaching signal "4" teaching that the motion is a fourth motion, and a combination of feature data obtained from a biological signal generated from a fifth motion and teaching data 5 (0.0, 0.0, 0.0, 0.0, 1.0) corresponding to teaching signal "5" teaching that the motion is a fifth motion when information to be identified is a motion of an organism, the first node of the output layer of the neural network 300 is associated with the first motion, the second node is associated with the second motion, the third node is associated with the third motion, the fourth node is associated with the fourth motion, and the fifth node is associated with the fifth motion. Examples of ideal outputs of the neural network 300 with weighting coefficients for each node calculated in this manner include an output of 1 by the first node of the output layer and an output of 0 by the other nodes when feature data obtained from a biological signal upon performing the first motion is inputted. However, an ideal output is actually hardly ever obtained due to the effect of noise or the like that coexists with a biological signal. In actuality, one or more nodes of the output layer would output a value in the range of 0 to 1. The value of each node of the output layer corresponds to the degree of similarity between the inputted feature data and each teaching data corresponding to a motion to which each node is associated. If, for example, the output is (0.0, 0.2, 0.0, 0.8, 0.0), this indicates that inputted feature data is slightly similar to teaching data corresponding to the second motion associated with the second node, and is more similar to teaching data corresponding to the fourth motion associated with the fourth node, but are not similar to teaching data corresponding to motions associated with other nodes. If, for example, the output is (0.0, 0.0, 0.6, 0.0, 0.6), this indicates that inputted feature data is similar to both teaching data corresponding to the third motion associated with the third node and teaching data corresponding to the fifth motion associated with the fifth node, but are not similar to teaching data corresponding to motions associated with other nodes.

Referring again to FIG. 2, the second determination means 223 is configured to determine information represented by a biological signal based on a plurality of degrees of similarity within a predetermined period in degrees of similarity stored in a buffer of the memory unit 230. For example, the second determination means 223 determines a degree of similarity with high intensity of appearance as the "likely output" from a plurality of degrees of similarity within a predetermined period in the degrees of similarity chronologically stored in the buffer of the memory unit 230, and determines information indicated by teaching data corresponding to said degree of similarity as information represented by a biological signal from which feature data originates.

The memory unit 230 comprises a buffer for temporarily storing information. A buffer can, for example, temporarily store degrees of similarity determined by the first determination means 222 for each time in chronological order. A buffer can, for example, delete old data once a certain amount of data is stored, or delete data after a certain period of time has passed after storage.

FIG. 4 shows an example of a data configuration of an output vector indicating the degrees of similarity with each teaching data stored in a buffer of the memory unit 230. The value of each component of an output vector indicates the degree of similarity with corresponding teaching data.

The buffer of the memory 230 chronologically stores output vectors for each time. For example, if the degrees of similarity with each teaching data 0 to 9 at time 1 are determined to be (0.0, 0.0, 0.2, 0.0, 0.5, 0.7, 0.0, 0.0, 0.0, 0.0) by the first determination means 222, the results are stored as an output vector indicating the degree of similarity with each teaching data at time 1, and if the degrees of similarity with each teaching data 0 to 9 at time 2 are determined to be (0.0, 0.0, 0.2, 0.0, 0.0, 0.7, 0.9, 0.0, 0.0, 0.0), the results are stored as an output vector indicating the degree of similarity with each teaching data at time 2, and so on. The time and output vector are stored each time a degree of similarity is determined by the first determination means 222 (see for example FIG. 4).

The example presented in FIG. 1 shows the biological signal detection means 100 and the computer apparatus 200 to be separate constituent elements, but the present invention is not limited thereto. The biological signal detection means 100 and the computer apparatus 200 can also be configured as a single constituent element.

In the example presented in FIG. 1, the database unit 250 is provided external to the computer apparatus 200, but the present invention is not limited thereto. The database unit 250 can also be provided inside the computer apparatus 200. At this time, the database unit 250 can be implemented by the same storage means as the storage means implementing the memory unit 230, or implemented by storage means that is different from the storage means implementing the memory unit 230. In either case, the database unit 250 is configured as a storage unit for the computer apparatus 200. The configuration of the database unit 250 is not limited to a specific hardware configuration. For example, the database unit 250 can be comprised of a single hardware component or a plurality of hardware components. For example, the database unit 250 can be configured as an external hard disk apparatus of the computer apparatus 200, or as cloud storage connected via a network.

In the example presented in FIG. 2, each constituent element of the computer apparatus 200 is provided within the computer apparatus 200, but the present invention is not limited thereto. Any of the constituent elements of the computer apparatus 200 can be provided external to the computer apparatus 200. For example, if each of the processor unit 220 and the memory unit 230 is configured as separate hardware components, each hardware component can be connected via any network. In this regard, any type of network can be used. For example, each hardware component can be connected via LAN, connected wirelessly, or connected with a wired connection.

While the aforementioned examples describe that the biological signal detection means 100 extracts a scalar quantity from a detected biological signal and outputs the scalar quantity if the detected biological signal is coordinate dependent, the computer apparatus 200 configured to extract a scalar quantity from a biological signal received from the biological signal detection means 100 is also within the scope of the present invention.

3. Processing for Identifying Information Represented by Biological Signal of the Invention FIG. 5 shows an example of the processing for identifying information represented by a biological signal of the invention. This processing is performed in the system 10.

It is assumed that teaching data corresponding to a teaching signal inputted during the learning stage is stored while being associated with inputted feature data in the database unit 250, and the weighting coefficient of each node of the hidden layer of the neural network 300 shown in FIG. 3 is calculated based on a combination of feature data and teaching data stored in the database unit 250.

In step S501, the detection unit 110 of the biological signal detection means 100 detects a biological signal. The detection unit 110 detects, for example, a myoelectric signal of an organism, a cardioelectric signal of an organism, or a brainwave of an organism. If the detection unit 110 detects a biological signal, the transmission unit 120 of the biological signal detection means 100 transmits the detected biological signal to the computer apparatus 200.

If the receiver unit 210 of the computer apparatus 200 receives a biological signal from the biological signal detection means 100, the receiver unit 210 provides the received biological signal to the processor unit 220. In this regard, the receiver unit 210 can be configured to, for example, sequentially provide biological signals to the processor unit 220 each time a biological signal is received, or temporarily store received biological signals in the memory unit 230 and provide the processor unit 220 with the signals at once after a certain amount of data is accumulated. Once the processor unit 220 is provided with a biological signal, the procedure proceeds to step S502.

In step S502, the analysis means 221 of the processor unit 220 of the computer apparatus 200 analyzes the detected biological signal and outputs feature data. The analysis means 221 outputs feature data by performing analysis and processing including smoothing, mathematical analysis such as frequency analysis, or parameter determination. The analysis means 221 can be configured to process feature data at this time by, for example, applying a weighting coefficient to a time series or frequency band of the outputted feature data.

In step S503, the first determination means 222 of the processor unit 220 of the computer apparatus 200 determines degrees of similarity between feature data outputted in step S502 and each of the plurality of teaching data. For example, the first determination means 222 inputs the feature data outputted in step S502 into the neural network 300 shown in FIG. 3, and determines the degrees of similarity between feature data and each of the plurality of teaching data from an output of the neural network 300.

The first determination means 222 can be configured, for example, to extract a part of feature data outputted in step S502 and input only the extracted feature data into the neural network 300 instead of inputting all of the feature data outputted in step S502 into the neural network 300. This can reduce the amount of computation in processing at a later stage to prevent a decrease in the operational speed in the processing at the later stage. At this time, the first determination means 222 can extract feature data uniformly or non-uniformly. If feature data is extracted non-uniformly, the feature data is preferably extracted with an unbalanced weighting so that the portion of the feature data to be focused on is mainly extracted. This can prevent decreased precision in the processing at a later stage due to extraction. Such extraction of feature data enables both high operational speed and precision in the processing at a later stage.

Once the first determination means 222 determines the degree of similarity, the procedure proceeds to step S504.

In step S504, the buffer of the memory unit 230 of the computer apparatus 200 chronologically stores the degrees of similarity determined in step S503 for each time. For example, the buffer of the memory unit 230 chronologically stores an output vector indicating degrees of similarly as shown in FIG. 4 for each time. The processor unit 220 is preferably configured to repeat step S501 to step S504 until a predetermined amount of data is stored in the buffer. This enables the use of a sufficient amount of data for degrees of similarity in the processing at a later stage and enhancement in precision of processing at a later stage. Once the buffer stores a degree of similarity, the processing proceeds to step S505.

In step S505, the second determination means 223 of the processor unit 220 of the computer apparatus 200 determines information represented by a biological signal based on a plurality of degrees of similarity within a predetermined period in chronological degrees of similarity stored in a buffer. The predetermined period can be any period, with the last time at which a degree of similarity is stored in a buffer being the end point. The predetermined period is, for example, any period of time within the range of about 10 ms to about 220 ms. The predetermined period is for example about 80 ms to about 220 ms. This is because the simple reaction time of humans is about 220 ms, so that it is difficult to change a motion being performed to another motion in less time than the simple reaction time. A predetermined period can be, for example, about 80 ms, about 200 ms, or the like. This is because a longer predetermined period would improve stability of outputs, whereas a delay would be greater so that responsiveness would be lower, and a delay greater than 200 ms would lead to temporal inconsistency in self-body recognition. The predetermined period can be appropriately determined by those skilled in the art in accordance with, for example, the application, application program used, user needs, or the like while considering the trade-off between the stability of outputs and human reaction time. When used for example in a finger rehabilitation application described below, the predetermined period can be greater than 220 ms (e.g., about 220 to about 400 ms, such as about 300 ms, about 350 ms, or about 400 ms). This is because the time it takes to change a motion being performed to another motion is longer for paralyzed patients as compared to healthy individuals.

For example, the second determination means 223 can be configured to calculate a computed value for each of a plurality of teaching data based on a plurality of degrees of similarity within a predetermined period and determine information represented by a biological signal based on the computed value. For example, the second determination means 223 can be configured to extract teaching data corresponding to the highest computed value among the obtained computed values and determine information indicated by the extracted teaching data as information represented by a biological signal. A computed value can be a value calculated by a known computation method or a computation method that can be conceived by those skilled in the art. A computed value can be, for example, a total value. As used herein, "total value" in the determination of information represented by a biological signal is understood by those skilled in the art as a concept that naturally encompasses "mean value". Specifically, the concept of calculating a total value for each of the plurality of teaching data and extracting teaching data corresponding to the highest total value thereamong encompasses the concept of calculating a mean value for each of the plurality of teaching data and extracting teaching data corresponding to the highest mean value thereamong. A computed value can be, for example, a probability or frequency of occurrence of a specific degree of similarity. The probability of occurrence of a specific degree of similarity is a value indicating the probability of a specific degree of similarity occurring within a predetermined period. The frequency of occurrence of a specific degree of similarity can be a value indicating how much a specific degree of similarity occurred within a predetermined period. In this regard, a specific degree of similarity can be, for example, the highest degree of similarity in an output vector or a degree of similarity at or above a threshold value in an output vector. If, for example, 5 output vectors are outputted within a predetermined period, and the highest degree of similarity is attained for a certain teaching data in 3 out of 5 output vectors, the frequency of occurrence is 3 and the probability of occurrence is ⅗.

A certain number (e.g., one) of lowest numerical values can be excluded from calculation for each of a plurality of teaching data in the calculation of a computed value (e.g., total value (mean value)). The lowest numerical value in this regard can be the lowest numerical value among numerical values that are not 0.

Alternatively, the second determination means 223 can determine information indicated by teaching data corresponding to a computed value exceeding a predetermined threshold value as information represented by a biological signal. If there is no computed value exceeding a predetermined threshold value at this time, the information would be unidentifiable. The information can also be unidentifiable if there are a plurality of computed values exceeding a predetermined threshold value. Alternatively, if there are a plurality of computed values exceeding a predetermined value, each information indicated by each teaching data corresponding to a plurality of computed values exceeding a predetermined threshold value can be determined as information represented by a biological signal. This is, for example, a case where a plurality of motions to be identified as concurrently performed, a case wherein a plurality of conditions to be identified are concurrently occurring, or the like. If, for example, motions indicated by each teaching data corresponding to two computed values exceeding a predetermined threshold value are "wrist bending motion" and "hand grasping motion", it is presumed that a composite motion of bending a wrist while grasping a hand is being performed, and "wrist bending motion" and "hand grasping motion" can be determined as motions represented by a biological signal. If, for example, motions indicated by each teaching data corresponding to two total values exceeding a predetermined threshold value are "hand grasping motion" and "wrist rotating motion", it is presumed that a composite motion of rotating a wrist while grasping a hand (e.g., motion of holding and turning a door knob) is being performed, and "hand grasping motion" and "wrist rotating motion" can be determined as motions represented by a biological signal. The second determination means 223 can identify any composite motion among motions of the entire body in accordance with the detected biological signal. If at least two of a plurality of motions are contradictory to one another (e.g., "hand opening motion" and "hand grasping motion"), the result can be deemed unidentifiable, or the system can be controlled as if muscle forces are exerted against each other, with the joint being rigid.

Any value can be set as a predetermined threshold value. While a higher predetermined threshold value leads to higher precision and stability, the percentage of cases with unidentifiable result would also be high, resulting in poor responsiveness. For example, a predetermined threshold value can be fixed value or a variable. If a predetermined threshold value is a variable, the predetermined threshold value can be, for example, a given ratio (e.g., 90% to 60%, 80% to 60%, 70% to 60%, such as 65%) with respect to the maximum value of the total value. For example, a predetermined value can be determined in accordance with the total number of data for a plurality of degrees of similarity within a predetermined period. If, for example, there is no total value exceeding a predetermined threshold value, the predetermined threshold value can be reduced or increased until there is at least one total value exceeding the threshold value. If, for example, there are a plurality of total values exceeding a threshold value, the predetermined threshold value can be increased until there is one total value exceeding the predetermined threshold value.

For example, a predetermined threshold value can be determined in accordance with the biological signal to be detected. A predetermined threshold value can be determined, for example, in accordance with a location where a biological signal is detected. For example, a predetermined threshold value used upon detection of a biological signal from an arm for identifying a hand motion and a predetermined threshold value used upon detection of a biological signal from a leg for identifying a walking motion can be the same or different values.

The precision of information represented by a biological signal identified by the aforementioned processing improved significantly as compared to the precision for identifying information represented by a biological signal directly from a degree of similarity outputted in step S503. While the precision for identifying information represented by a biological signal directly from a degree of similarity outputted in step S503 was about 80%, the precision of information represented by a biological signal identified by the aforementioned processing was very high, reaching a percentage in the high 90s.

As an example, processing of the system 10 when a user performs a motion corresponding to teaching data 5 among motions corresponding to teaching data 0 to 9 is described with reference to FIGS. 6A to 6C. It is assumed that a user is performing a motion corresponding to teaching data 5 from time 1 to time 5. In this regard, the processing at time 5 is described. It is assumed that the interval between each time is 20 ms, and the predetermined period is 100 ms. It is assumed that output vectors for time 1 to time 4 are already stored in the buffer of the memory unit 230 as shown in FIG. 6A.

In step S501, the detection unit 110 of the biological signal detection means 100 detects a biological signal originating from a motion performed by a user.

In step S502, the analysis means 221 of the processor unit 220 of the computer apparatus 200 analyzes the detected biological signal and outputs feature data.

In step S503, the first determination means 222 of the processor unit 220 of the computer apparatus 200 determines degrees of similarity between the feature data outputted in step S502 and each of teaching data 0 to 9. Inputting the feature data outputted in step S502 into the neural network 300 results in degrees of similarity (0.0, 0.9, 0.2, 0.0, 0.0, 0.7, 0.0, 0.0, 0.0, 0.0) with each of teaching data 0 to 9 as outputs.

In step S504, the buffer of the memory unit 230 of the computer apparatus 200 chronologically stores the degrees of similarity determined in step S503. The buffer of the memory unit 230 would chronologically store output vectors for time 1 to time 5 for each time, as shown in FIG. 6B.

In step S505, the second determination means 223 of the processor unit 220 of the computer apparatus 200 determines a motion represented by a biological signal originating from a motion performed by a user based on a plurality of degrees of similarity within a predetermined period in chronological degrees of similarity stored in the buffer. First, the second determination means 223 obtains a total value by totaling degrees of similarity for time 1 to time 5 corresponding to the predetermined period for each teaching data, as shown in FIG. 6B. Next, the second determination means 223 determines the motion indicated by teaching data for "5" corresponding to the highest total value as the motion represented by a biological signal detected at time 5. Alternatively, if the predetermined threshold value is 2.5, the second determination means 223 determines the motion indicated by teaching data for "5" corresponding to a total value exceeding a predetermined threshold value as the motion represented by a biological signal detected at time 5. In this manner, the system 10 of the invention can appropriately identify the motion performed by a user.

If, for example, a motion represented by a biological signal were to be identified directly from the degrees of similarity obtained in step S503, the motion would be incorrectly identified as the motion corresponding to teaching data "1" because the teaching data corresponding to the highest degree of similarity would be teaching data "1". In contrast, the system 10 of the invention determines a motion represented by a biological signal based on a plurality of degrees of similarity within a predetermined period in chronological degrees of similarity stored in a buffer, so that a motion represented by a biological signal can be identified with very high precision.

The processing performed when a user performs a motion corresponding to teaching data 5 at time 6 is also the same.

In step S501, the detection unit 110 of the biological signal detection means 100 detects a biological signal originating from a motion performed by a user. In step S502, the analysis means 221 of the processor unit 220 of the computer apparatus 200 analyzes the detected biological signal and outputs feature data. In step S503, the first determination means 222 of the processor unit 220 of the computer apparatus 200 determines degrees of similarity between the feature data outputted in step S502 and each of teaching data 0 to 9. Inputting the feature data outputted in step S502 into the neural network 300 resulted in degrees of similarity (0.0, 0.0, 0.2, 0.0, 0.0, 0.7, 0.9, 0.0, 0.0, 0.0) with each of teaching data 0 to 9 as outputs.

In step S504, the buffer of the memory unit 230 of the computer apparatus 200 chronologically stores the degrees of similarity determined in step S503. The buffer of the memory unit 230 chronologically stores output vectors for time 1 to time 6 for each time as shown in FIG. 6C.

In step S505, the second determination means 223 of the processor unit 220 of the computer apparatus 200 determines a motion represented by a biological signal originating from a motion performed by a user based on a plurality of degrees of similarity within a predetermined period in chronological degrees of similarity stored in the buffer. First, the second determination means 223 obtains a total value by totaling degrees of similarity for time 2 to time 6 corresponding to the predetermined period for each teaching data, as shown in FIG. 6C. Next, the second determination means 223 extracts teaching data for "5" corresponding to the highest total value and determines the motion indicated by the extracted teaching data for "5" as the motion represented by a biological signal detected at time 6. Alternatively, if the predetermined threshold value is 2.5, the second determination means 223 determines the motion indicated by teaching data for "5" corresponding to a total value exceeding a predetermined threshold value as a motion represented by a biological signal detected at time 6. In this manner, the system 10 of the invention can appropriately identify the motion performed by a user.

If, for example, a motion represented by a biological signal were to be identified directly from the degrees of similarity obtained in step S503, the motion would be incorrectly identified as the motion corresponding to teaching data 6 because the teaching data corresponding to the highest degree of similarity would be teaching data 6. In contrast, the system 10 of the invention determines a motion represented by a biological signal based on a plurality of degrees of similarity within a predetermined period in chronological degrees of similarity stored in a buffer, so that a motion represented by a biological signal can be similarly identified with very high precision at time 6.

As another example, processing of the system 10 when a user performs a composite motion of a motion corresponding to teaching data 3 and a motion corresponding to teaching data 7 among motions corresponding to teaching data 0 to 9 is described with reference to FIGS. 6D to 6F. It is assumed that a user is performing a motion corresponding to teaching data 3 and a motion corresponding to teaching data 7 from time 1 to time 5. In this regard, the processing at time 5 is described. It is assumed that the interval between each time is 20 ms, and the predetermined period is 100 ms. It is assumed that output vectors for time 1 to time 4 are already stored in the buffer of the memory unit 230 as shown in FIG. 6D.

In step S501, the detection unit 110 of the biological signal detection means 100 detects a biological signal originating from a motion performed by a user.

In step S502, the analysis means 221 of the processor unit 220 of the computer apparatus 200 analyzes the detected biological signal and outputs feature data.

In step S503, the first determination means 222 of the processor unit 220 of the computer apparatus 200 determines degrees of similarity between the feature data outputted in step S502 and each of teaching data 0 to 9. Inputting the feature data outputted in step S502 into the neural network 300 results in degrees of similarity (0.0, 0.0, 0.2, 0.9, 0.2, 0.1, 0.0, 0.8, 0.0, 0.9) with each of teaching data 0 to 9 as outputs.

In step S504, the buffer of the memory unit 230 of the computer apparatus 200 chronologically stores the degrees of similarity determined in step S503. The buffer of the memory unit 230 would chronologically store output vectors for time 1 to time 5 for each time, as shown in FIG. 6E.

In step S505, the second determination means 223 of the processor unit 220 of the computer apparatus 200 determines a motion represented by a biological signal originating from a motion performed by a user based on a plurality of degrees of similarity within a predetermined period in chronological degrees of similarity stored in the buffer. First, the second determination means 223 obtains a total value by totaling degrees of similarity for time 1 to time corresponding to the predetermined period for each teaching data, as shown in FIG. 6E. Next, the second determination means 223 determines the motion indicated by teaching data exceeding a predetermined threshold value as the motion represented by a biological signal detected at time 5. If, for example, the predetermined threshold value is a fixed value 3.5, the second determination means 223 determines the motion indicated by teaching data "3" and the motion indicated by teaching data "7" corresponding to a total value exceeding a predetermined threshold value as a motion represented by a biological signal detected at time 5. In this manner, the system 10 of the invention can appropriately and simultaneously identify the composite motion performed by a user.

If, for example, a motion represented by a biological signal were to be identified directly from the degrees of similarity obtained in step S503, the motion would be incorrectly identified as the motion corresponding to teaching data "9" because the teaching data corresponding to the highest degree of similarity would be teaching data "9". In contrast, the system 10 of the invention determines a motion represented by a biological signal based on a plurality of degrees of similarity within a predetermined period in chronological degrees of similarity stored in a buffer, so that a motion represented by a biological signal can be identified with very high precision, even for a composite motion.

The processing performed when a user performs a motion corresponding to teaching data 5 at time 6 is also the same.

In step S501, the detection unit 110 of the biological signal detection means 100 detects a biological signal originating from a motion performed by a user. In step S502, the analysis means 221 of the processor unit 220 of the computer apparatus 200 analyzes the detected biological signal and outputs feature data. In step S503, the first determination means 222 of the processor unit 220 of the computer apparatus 200 determines degrees of similarity between the feature data outputted in step S502 and each of teaching data 0 to 9. Inputting the feature data outputted in step S502 into the neural network 300 resulted in degrees of similarity (0.2, 0.9, 0.2, 0.7, 0.3, 0.1, 0.0, 0.7, 0.0, 0.1) with each of teaching data 0 to 9 as outputs.

In step S504, the buffer of the memory unit 230 of the computer apparatus 200 chronologically stores the degrees of similarity determined in step S503. The buffer of the memory unit 230 chronologically stores output vectors for time 1 to time 6 for each time as shown in FIG. 6F.

In step S505, the second determination means 223 of the processor unit 220 of the computer apparatus 200 determines a motion represented by a biological signal originating from a motion performed by a user based on a plurality of degrees of similarity within a predetermined period in chronological degrees of similarity stored in the buffer. First, the second determination means 223 obtains a total value by totaling degrees of similarity for time 2 to time 6 corresponding to the predetermined period for each teaching data, as shown in FIG. 6F. Next, the second determination means 223 determines the motion indicated by teaching data exceeding a predetermined threshold value as the motion represented by a biological signal detected at time 6. If, for example, the predetermined threshold value is a fixed value 3.5, the second determination means 223 determines the motion indicated by teaching data "3" and the motion indicated by teaching data "7" corresponding to a total value exceeding a predetermined threshold value as a motion represented by a biological signal detected at time 6. In this manner, the system 10 of the invention can appropriately and simultaneously identify the composite motion performed by a user.

If, for example, a motion represented by a biological signal were to be identified directly from the degrees of similarity obtained in step S503, the motion would be incorrectly identified as the motion corresponding to teaching data "1" because the teaching data corresponding to the highest degree of similarity would be teaching data "1". In contrast, the system 10 of the invention determines a motion represented by a biological signal based on a plurality of degrees of similarity within a predetermined period in chronological degrees of similarity stored in a buffer, so that a motion represented by a biological signal can be similarly identified with very high precision at time 6, even for a composite motion.

4. Application Example

The system 10 of the invention can be used in any application wherein it is useful to detect a biological signal resulting in some type of an output, but the system is preferably for, but not limited to, finger rehabilitation, swallow diagnosis, wheelchair, prosthetic hand, prosthetic arm, prosthetic foot, robot, upper limb assisting apparatus, lower limb assisting apparatus, or trunk assisting apparatus. If, for example, the system is for a robot, the system can be applied to, for example, the entire robot or a part of a robot such as a robot arm or a robot hand.

The system 10 of the invention can comprise, in accordance with the application, wearing means for wearing the system on a part of the body of a subject whose biological signal is to be analyzed. Such a part of the body can be, but is not limited to, the upper limb, abdomen, neck, lower limb, or back of the subject emitting a biological signal. A part of the body can be any part of the body. Wearing means can be any wearing means, such as a belt or sticker for wearing the system on a part of the body of a subject. If, for example, the system 10 of the invention is for a robot arm, the system can be configured to detect a myoelectric signal of a muscle of an upper limb and move the robot arm based on information represented by the detected myoelectric signal. In such a case, a user can, for example, make a robot arm mimic a motion intended by the user by using the system 10 of the invention. Since the system 10 of the invention can identify not only a simple motion but also a composite motion, the system can make a robot arm mimic even a composite motion with high precision. Alternatively, if the system 10 of the invention is for robot arms, the system can be configured to detect a myoelectric signal of a muscle of a body part other than the forearm (e.g., facial muscle) and move the robot arm based on information represented by the detected myoelectric signal. In such a case, a user can, for example, operate a robot arm by the user's own predetermined motion as a command by using the system 10 of the invention. This enables operation of a robot arm even by, for example, patients with upper limb paralysis. Since the system 10 of the invention can identify not only a simple motion but also a composite motion, the number of commands for operation can be increased compared to operations using a simple motion as a command. Specifically, use of a composite motion as a command enables a robot arm to perform more motions with fewer types of user motions.

In a preferred embodiment, the system 10 of the invention can be applied to, for example, a finger rehabilitation apparatus.

For a patient with paralysis in a finger in need of rehabilitation thereof (e.g., stroke patient), the biological signal level would be lower. Thus, the precision of identifying a motion represented by a biological signal is lower as compared to healthy individuals. However, a motion represented by a biological signal can be identified with very high precision with the system 10 of the invention, so that the identification precision can be enhanced to a level that is usable in rehabilitation even if the biological signal level is low. The system 10 of the invention can precisely and simultaneously identify not only a simple motion of a finger, but also a composite motion of a finger. For this reason, the efficiency and effect of rehabilitation of a finger is dramatically improved by accurately and rapidly identifying a motion intended by a patient and correctly and immediately assisting the intended motion. For example, it is known that plasticity of the brain is promoted and recovery of the paralyzed function is promoted by actually performing and repeating a motion intended by a patient.

A finger rehabilitation apparatus comprising the system 10 of the invention comprises wearing means that enables the biological signal detection means 100 to be worn on the skin of an upper limb of a user. For example, wearing means can be any means such as a belt or sticker for wearing the detection unit 111 of the biological signal detection means 100 on the skin of an upper limb (e.g., upper arm or forearm) of a user.

For example, an output from a finger rehabilitation apparatus can be displayed on display means such as a display and presented to a rehabilitation trainer. A rehabilitation trainer can provide pertinent rehabilitation guidance based on an output from a finger rehabilitation apparatus, leading to efficient and effective rehabilitation.

A finger rehabilitation apparatus comprising the system 10 of the invention can comprise a finger movement assisting apparatus worn on a finger of a user. A finger movement assisting apparatus is configured to act on a finger of a user so as to assist the movement of the finger of the user. A finger movement assisting apparatus can be configured, for example, to drive a finger joint with a pneumatic actuator or to drive a finger joint by the torque of a motor.

A finger movement assisting apparatus can be, for example, a finger movement assisting apparatus 700 shown in FIGS. 7A and 7B.

FIG. 7A shows the outer appearance of the finger movement assisting apparatus 700. FIG. 7B shows the finger movement assisting apparatus 700 worn on a finger of a user.

The finger movement assisting apparatus 700 comprises a main body 710, a palm bolt 720 extending from the main body 710, an arm 730, and a finger bolt 740 extending from the arm 730. The arm 730 is configured to be pivotable with respect to the main body 710. The arm 730 can be configured to be pivoted by a motor, by a pneumatic actuator, or by a wire.

In a finger rehabilitation apparatus comprising the system 10 of the invention, an output from the system 10 of the invention can be provided to the finger movement assisting apparatus. A finger movement assisting apparatus acts to assist the motion intended by a patient based on an output from a finger rehabilitation apparatus. For example, an output from the system 10 of the invention can be provided to the finger movement assisting apparatus 700. If the finger movement assisting apparatus 700 is worn on a finger as shown in FIG. 7B, the finger bolt 740 assists the motion of the finger by a pivotal motion of the arm 730. For example, the finger bolt 740 pushes the finger up by a pivotal motion of the arm 730, which can assist the hand opening motion of a user. In this manner, patients can rehabilitate by their own will, leading to efficient and effective rehabilitation.

In another preferred embodiment, the system 10 of the invention can be applied to, for example, a swallow diagnosis apparatus.

If a myoelectric signal is to be obtained around the neck, it is difficult to identify the motion from which the myoelectric signal has originated because a plurality of myoelectric signals indicating activity of a plurality of muscles coexist. Thus, the identification precision decreases. However, since a motion represented by a biological signal can be identified at very high precision with the system 10 of the invention, identification precision can be improved to a level where swallowing impairment can be diagnosed, even if myoelectric signals coexist. The system 10 of the invention can not only precisely identify simple motions in jaw and oral movements, but also composite motions in jaw and oral movements. This enables correct swallow diagnosis based on a myoelectric signal, for example, by identifying whether the motion is swallowing motion when suffering from a swallowing impairment or a healthy swallowing motion without a swallowing impairment.

A swallow diagnosis apparatus comprising the system 10 of the invention comprises wearing means that enables the biological signal detection means 100 to be worn on the skin of a neck of a user. Wearing means can be any means such as a belt or a sticker for wearing the detection unit 111 of the biological signal detection means 100 on the skin of a neck of a user. A swallow diagnosis apparatus comprising the system 10 of the invention can comprise means that enables the biological signal detection means 100 to be in contact with, without fixing the means to, the skin of a neck of a user in addition or in place of the wearing means. Such means can detect a biological signal of a patient, for example, by pressing the means onto a patient in the same manner as a stethoscope.

For example, an output from a swallow diagnosis apparatus can be displayed on display means such as a display and presented to a physician. A physician can render an accurate diagnosis based on an output from a swallow diagnosis apparatus. Alternatively, an output from a swallow diagnosis apparatus can be displayed on a display or the like and presented to the users themselves. This enables users to accurately self-diagnose a swallowing impairment based on an output from a swallow diagnosis apparatus.

EXAMPLES

Example 1. Identification of Myoelectric Signal on the Skin of an Upper Limb

A subject (healthy male in his 20s) was asked to wear a myoelectric sensor on the upper limb and move firmly with force to study the corresponding relationship between identification of a myoelectric signal and motion. The myoelectric sensor comprised an amp unit, a 500 Hz low pass filter, a 10 Hz high pass filter, and a 50 Hz notch filter. The experiment was conducted with 80 ms as the predetermined period.

The test results are shown in FIGS. 8 and 9. FIGS. 8(a) and 9(a) are graphs of results of processing using the system 10 of the invention. FIGS. 8(b) and 9(b) are graphs of results of identifying directly from degrees of similarity obtained in step S503, i.e., from the output of the neural network 300. FIGS. 9(a) to 9(b) are diagrams expanding the dotted line portions shown in FIGS. 8(a) to 8(b).

The vertical axis of the graphs indicates motion ID. 0 is "no motion", 1 is "wrist supine motion", 3 is "wrist bending motion", 4 is "wrist stretching motion", 5 is "fist clenching motion", 7 is "thumb bending motion", and 9 is "ring finger, pinky finger bending motion". It is assumed for the neural network 300 that a weighting coefficient of each node is calculated so that each node of an output layer is associated with a motion corresponding to a motion ID. The horizontal axis of the graphs is the number of execution steps. 50 steps were performed per second. Specifically, each step interval is 20 ms.

A subject performed motions in the order of "wrist supine motion" (motion ID: 1), "ring finger, pinky finger bending motion" (motion ID: 9), "thumb bending motion" (motion ID: 7), "wrist stretching motion" (motion ID: 4), "wrist bending motion" (motion ID: 3), and "fist clenching motion" (motion ID: 5).

The dotted lines in each graph indicate the ideal state of 100% identification rate.

As can be understood from FIG. 8, FIG. 8(a) is a graph that mostly follows the dotted lines. It can be understood that processing with the system 10 of the invention attained excellent identification rate.

As can be understood from FIG. 9, FIG. 9(a) is a graph that more closely follows the dotted lines than FIG. 9(b) even for the "wrist stretching motion" (motion ID: 4) which tends to be difficult to identify. It can be understood that the system 10 of the invention accurately identifies the motions represented by a myoelectric signal.

The identification rate is calculated from each graph. The identification rate of FIGS. 8(a) and 9(a) was 98.8%, and the identification rate of FIGS. 8(b) and 9(b) was 79.9%.

In this manner, the system 10 of the invention was demonstrated to be capable of identifying a motion represented by a biological signal at very high precision.

Example 2. Identification of Myoelectric Signal on the Skin of an Upper Limb of Subject with Low Myoelectric Signal Level A subject (healthy male in his 20s) was asked to wear a myoelectric sensor on the upper limb. The corresponding relationship between identification of a myoelectric signal and motion was studied in the same manner as Example 1, except for asking the subject to move with minimal force.

The test results are shown in FIGS. 10 and 11. FIGS. 10(a) and 11(a) are graphs of results from processing with the system 10 of the invention. FIGS. 10(b) and 11(b) are graphs of results from processing using the algorithm described below. FIGS. 10(c) and 11(c) are graphs of results of identifying directly from the degrees of similarity obtained in step S503, i.e., outputs of the neural network 300. FIGS. 11(a) to 11(c) are diagrams expanding the dotted line portions shown in FIGS. 10(a) to 10(c).

The algorithm used in FIGS. 10(b) and 11(b) is an algorithm for chronologically storing results of identifying directly from the degrees of similarity obtained in step S503, i.e., outputs of the neural network 300, for each time in a buffer, and determining an identification result with a share within the buffer equal to or greater than a threshold value as a motion represented by a myoelectric signal.

The vertical axis of the graphs indicates motion ID. 0 is "no motion", 1 is "wrist supine motion", 3 is "wrist bending motion", 4 is "wrist stretching motion", 5 is "fist clenching motion", 7 is "thumb bending motion", and 9 is "ring finger, pinky finger bending motion". It is assumed for the neural network 300 that a weighting coefficient of each node is calculated so that each node of an output layer is associated with a motion corresponding to a motion ID. The horizontal axis of the graphs is the number of execution steps. 50 steps were performed per second. Specifically, each step interval is 20 ms.

A subject performed motions in the order of "fist clenching motion" (motion ID: 5), "wrist bending motion" (motion ID: 3), "wrist stretching motion" (motion ID: 4), "thumb bending motion" (motion ID: 7), "ring finger, pinky finger bending motion" (motion ID: 9), and "wrist supine motion" (motion ID: 1).

The dotted lines in each graph indicate the ideal state of 100% identification rate.

As can be understood especially from FIG. 11, FIG. 11(a) is a graph that more closely follows the dotted lines than FIG. 11(b) even for the "thumb bending motion" (motion ID: 7), which tends to be difficult to identify with low myoelectric signal levels. It can be understood that the system 10 of the invention accurately identifies the motions represented by a myoelectric signal.

In this manner, the system 10 of the invention was demonstrated to be capable of identifying a motion represented by a biological signal at very high precision, even with a low biological signal level.

The present invention is not limited to the aforementioned embodiments. It is understood that the scope of the present invention should be interpreted solely from the scope of the claims. It is understood that those skilled in the art can implement an equivalent scope, based on the descriptions of the invention and common general knowledge, from the descriptions of the specific preferred embodiments of the invention.

INDUSTRIAL APPLICABILITY

The present invention is useful for providing a system for identifying information represented by a biological signal, which enables enhanced precision to identify a biological signal, and a finger rehabilitation apparatus and a swallow diagnosis apparatus comprising the same.

REFERENCE SIGNS LIST

10 System
100 Biological signal detection means

200 Computer apparatus
250 Database unit

The invention claimed is:

1. A computer apparatus for identifying information represented by a biological signal, the computer apparatus comprising:
receiver means for receiving a biological signal;
analysis means for analyzing the received biological signal and outputting feature data;
first determination means for determining output vectors indicating degrees of similarity between the feature data and each of a plurality of teaching data;
storage means for chronologically storing the output vectors for each time; and
second determination means for determining information represented by the biological signal based on a plurality of output vectors within a predetermined period in the chronological output vectors stored in the storage means, wherein the second determination means:
calculates computed values for each one of the plurality of teaching data by performing a computation on degrees of similarity indicated by each of corresponding chronological components of the plurality of output vectors within the predetermined period, wherein each of the degree of similarity on which the computation is performed has a value in a range of 0 to 1, wherein an end point of the predetermined period is a last time at which an output vector is stored in the storage means; and
determines the information represented by the biological signal based on the computed values.

2. The computer apparatus of claim 1, wherein the second determination means extracts teaching data corresponding to a highest computed value among the computed values and determines information indicated by the extracted teaching data as the information represented by the biological signal.

3. The computer apparatus of claim 1, wherein the second determination means extracts at least one teaching data corresponding to a computed value exceeding a predetermined threshold value among the computed values and determines information indicated by the extracted teaching data as the information represented by the biological signal.

4. The computer apparatus of claim 3, wherein the second determination means extracts a plurality of teaching data corresponding to computed values exceeding the predetermined threshold value among the computed values and determines information indicated by each of the plurality of extracted teaching data as the information represented by the biological signal.

5. The computer apparatus of claim 4, wherein the information represented by the biological signal indicates that a composite motion has been performed.

6. The computer apparatus of claim 1, wherein the computed values are total values.

7. The computer apparatus of claim 1, wherein the storage means is a buffer for temporarily storing information, and the output vectors are temporarily stored in the buffer.

8. The computer apparatus of claim 1, wherein the predetermined period is about 10 to 200 ms.

9. The computer apparatus of claim 1 for finger rehabilitation, for swallow diagnosis, for a wheelchair, for a prosthetic hand, for a prosthetic arm, for a prosthetic foot, for a robot, for an upper limb assisting apparatus, for a lower limb assisting apparatus, or for a trunk assisting apparatus.

10. A method for identifying information represented by a biological signal, the method comprising:
receiving a biological signal;
analyzing the received biological signal and outputting feature data;
determining output vectors indicating degrees of similarity between the feature data and each of a plurality of teaching data;
chronologically storing the output vectors for each time in a storage means; and
determining information represented by the biological signal based on a plurality of output vectors within a predetermined period in the chronological output vectors stored in the storage means, wherein determining information represented by the biological signal comprising:
calculating computed values for each one of the plurality of teaching data by performing a computation on degrees of similarity indicated by each of corresponding chronological components of the plurality of output vectors within the predetermined period, wherein each of the degrees of similarity on which the computation is performed has a value in a range of 0 to 1, wherein an end point of the predetermined period is a last time at which an output vector is stored in the storage means; and
determining the information represented by the biological signal based on the computed values.

11. A non-transitory storage medium storing a program for identifying information represented by a biological signal, the program is executed in a computer apparatus comprising a processor unit and a memory unit, the program cause the processor unit to perform a processing comprising:
receiving a biological signal;
analyzing the received biological signal and outputting feature data;
determining output vectors indicating degrees of similarity between the feature data and each of a plurality of teaching data;
chronologically storing the output vectors for each time in the memory unit; and
determining information represented by the biological signal based on a plurality of output vectors within a predetermined period in the chronological output vectors stored in the memory unit, wherein determining information represented by the biological signal comprising:
calculating computed values for each one of the plurality of teaching data by performing a computation on degrees of similarity indicated by each of corresponding chronological components of the plurality of output vectors within the predetermined period, wherein each of the degrees of similarity on which the computation is performed has a value in the range of 0 to 1, wherein an end point of the predetermined period is a last time at which an output vector is stored in the memory unit; and
determining the information represented by the biological signal based on the computed values.

* * * * *